United States Patent
Wegener

(10) Patent No.: US 9,744,498 B2
(45) Date of Patent: Aug. 29, 2017

(54) DISPOSABLE FLUID CIRCUITS AND METHODS FOR CELL WASHING WITH ON-LINE DILUTION OF CELL FEED

(71) Applicant: Fenwal, Inc., Lake Zurich, IL (US)

(72) Inventor: Christopher Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 908 days.

(21) Appl. No.: 13/708,874

(22) Filed: Dec. 7, 2012

(65) Prior Publication Data

US 2013/0092630 A1  Apr. 18, 2013

Related U.S. Application Data

(63) Continuation-in-part of application No. PCT/US2012/054859, filed on Sep. 12, 2012, and a continuation-in-part of application No. PCT/US2012/028522, filed on Mar. 9, 2012.

(60) Provisional application No. 61/537,856, filed on Sep. 22, 2011, provisional application No. 61/618,307, filed on Mar. 30, 2012, provisional application No. 61/636,411, filed on Apr. 20, 2012, provisional
(Continued)

(51) Int. Cl.
| | |
|---|---|
| *B01D 63/16* | (2006.01) |
| *A61M 1/36* | (2006.01) |
| *A61M 1/02* | (2006.01) |
| *A61M 1/26* | (2006.01) |
| *B01D 61/00* | (2006.01) |

(52) U.S. Cl.
CPC ............ *B01D 63/16* (2013.01); *A61M 1/0209* (2013.01); *A61M 1/0218* (2014.02); *A61M 1/0236* (2014.02); *A61M 1/265* (2014.02); *A61M 1/3693* (2013.01); *A61M 1/3696* (2014.02); *B01D 61/00* (2013.01); *B01D 2315/02* (2013.01)

(58) Field of Classification Search
CPC .............. A61M 1/0209; A61M 1/0218; A61M 1/0236; A61M 1/3696; A61M 1/3693; A61M 1/265; A61M 1/0272; A61M 1/0281; A61M 1/34; A61M 1/3403; A61M 1/342; A61M 1/3431; A61M 1/3434; A61M 1/3455; A61M 1/3633; A61M 1/3639; A61M 1/3687; A61M 1/3689; A61M 1/3692; B01D 63/16; B01D 61/00; B01D 2315/02
See application file for complete search history.

(56) References Cited

U.S. PATENT DOCUMENTS

| | | | |
|---|---|---|---|
| 4,806,247 A * | 2/1989 | Schoendorfer | ......... A61M 1/30 |
| | | | 210/321.68 |
| 4,851,126 A | 7/1989 | Schoendorfer | |

(Continued)

OTHER PUBLICATIONS

Written Opinion of the International Preliminary Examining Authority dated Feb. 4, 2014 for International Application No. PCT/US2012/054859.
(Continued)

*Primary Examiner* — David C Mellon
(74) *Attorney, Agent, or Firm* — Cook Alex Ltd.

(57) ABSTRACT

Systems and methods for the washing and processsing of biological fluid/biological cells are disclosed. The systems and methods prevent inadvertent target cell loss by monitoring pressure and providing for the dilution of the cell feed.

16 Claims, 27 Drawing Sheets

Related U.S. Application Data application No. 61/451,903, filed on Mar. 11, 2011, provisional application No. 61/538,558, filed on Sep. 23, 2011, provisional application No. 61/550,516, filed on Oct. 24, 2011.

(56) References Cited

U.S. PATENT DOCUMENTS

| | | | |
|---|---|---|---|
| 4,871,462 A * | 10/1989 | Fischel | B01D 63/16 210/321.64 |
| 4,944,883 A * | 7/1990 | Schoendorfer | A61M 1/30 210/194 |
| 5,055,198 A * | 10/1991 | Shettigar | A61M 1/02 210/104 |
| 5,364,526 A | 11/1994 | Matkovich | |
| 5,443,451 A | 8/1995 | Chapman et al. | |
| 5,665,061 A * | 9/1997 | Antwiler | A61M 1/3624 604/19 |
| 5,925,246 A * | 7/1999 | Lee | B01D 29/118 210/321.63 |
| 6,027,657 A | 2/2000 | Min et al. | |
| 6,518,010 B2 | 2/2003 | Gawryl et al. | |
| 2002/0128584 A1 | 9/2002 | Brown | |
| 2005/0059921 A1 * | 3/2005 | Tu et al. | 604/5.02 |
| 2005/0143712 A1 | 6/2005 | Mathias | |
| 2005/0274672 A1 * | 12/2005 | Tu | A61M 1/3496 210/645 |
| 2008/0108931 A1 | 5/2008 | Bobroff | |
| 2009/0045144 A1 * | 2/2009 | Cohen | B01D 61/025 210/745 |
| 2009/0211987 A1 | 8/2009 | Min | |
| 2013/0341291 A1 | 12/2013 | Wegener et al. | |
| 2014/0050615 A1 * | 2/2014 | Robinson | B30B 9/04 422/44 |
| 2014/0199680 A1 | 7/2014 | Min et al. | |

OTHER PUBLICATIONS

International Preliminary Report on Patentability dated May 19, 2014 for International Application No. PCT/US2012/054859.
International Search Report for International Application No. PCT/US2012/054859 dated May 22, 2013.

* cited by examiner

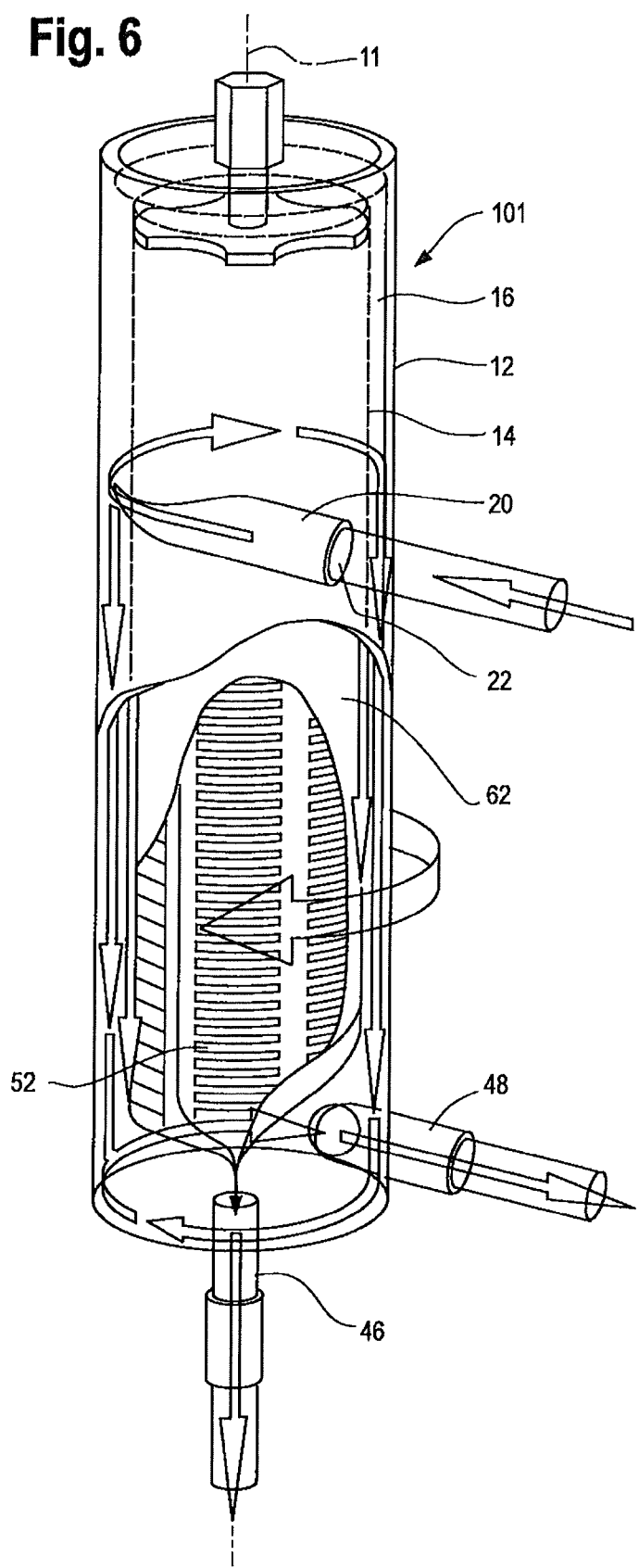

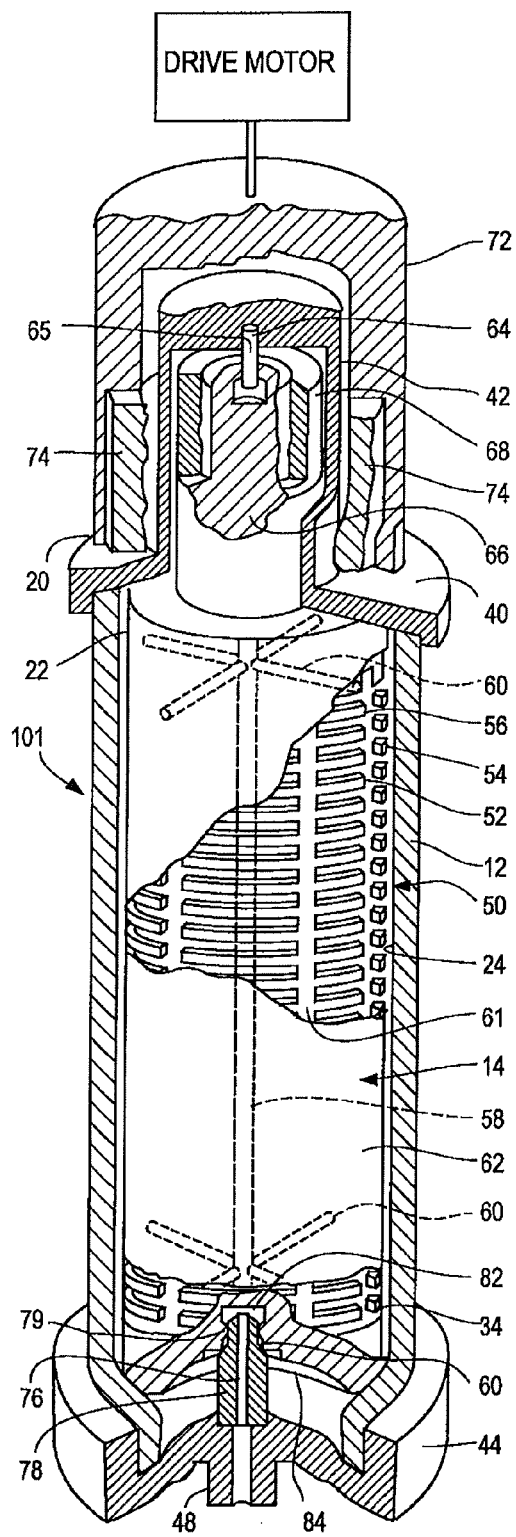
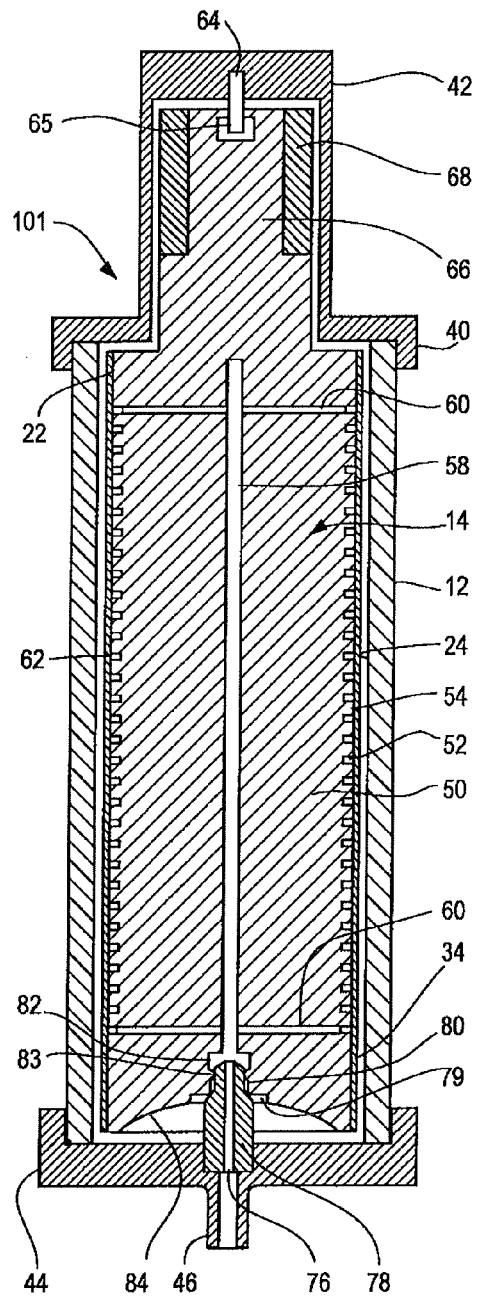
Fig. 7a
Fig. 7b

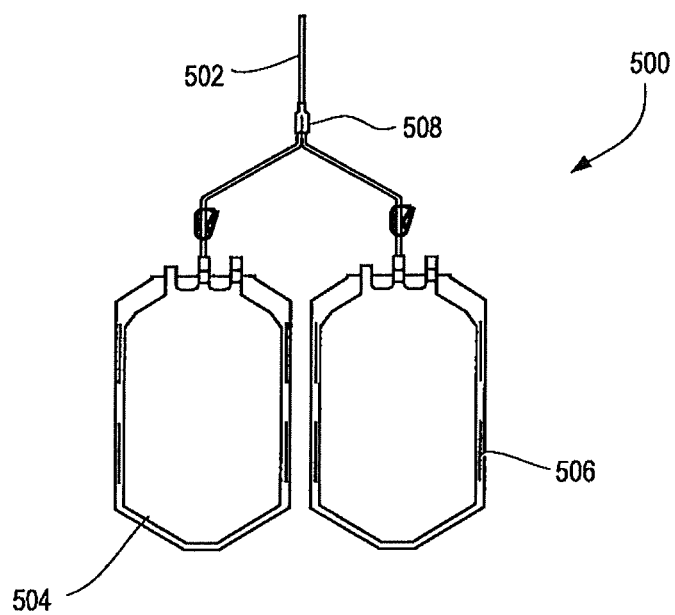

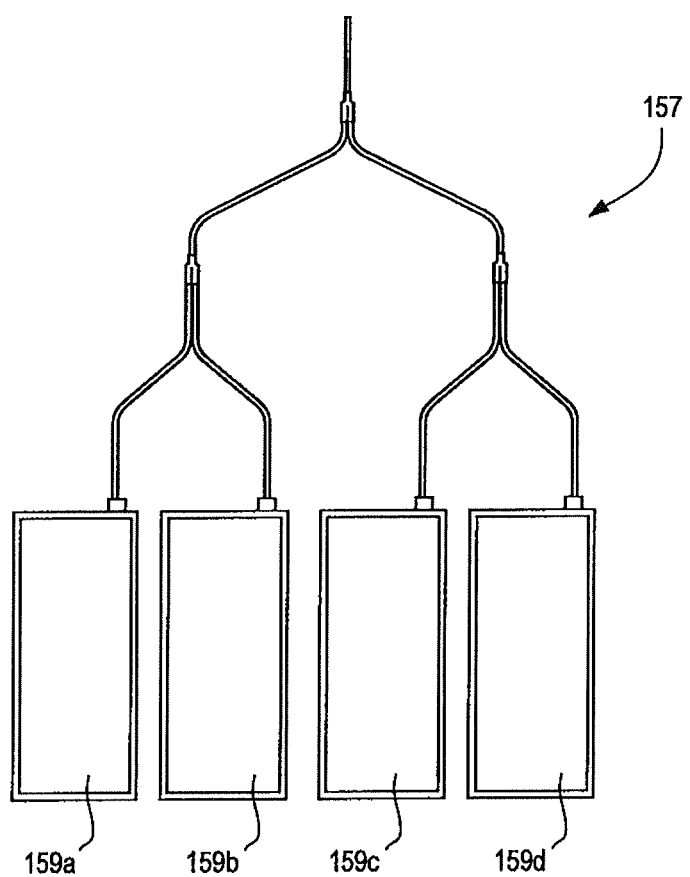

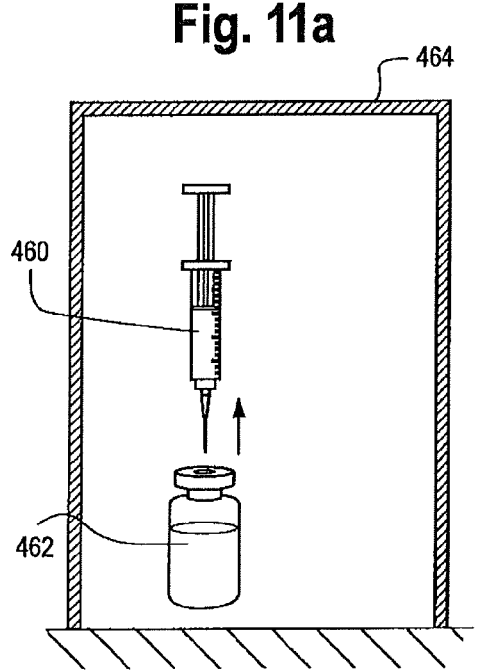
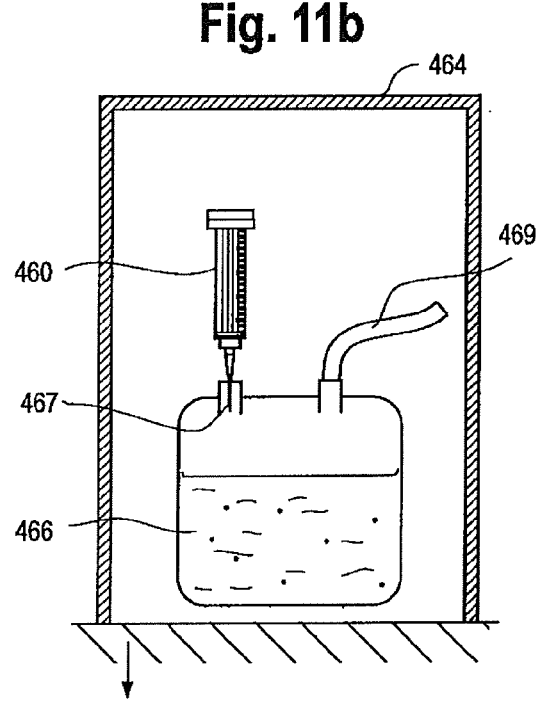
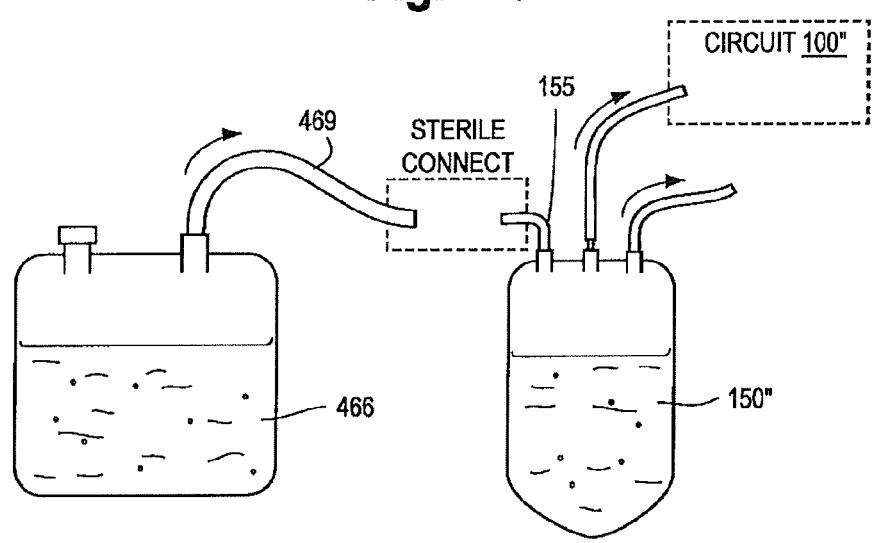

100%   10:1 CONCENTRATION   1:10 DILUTION   ~10%

10%   10:1 CONCENTRATION   1:10 DILUTION   ~1%

DISPOSABLE FLUID CIRCUITS AND METHODS FOR CELL WASHING WITH ON-LINE DILUTION OF CELL FEED

CROSS-REFERENCE TO RELATED APPLICATIONS

This application is a continuation-in-part of International Application No. PCT/US12/54859, filed Sep. 12, 2012, which claims the benefit of U.S. Provisional Patent Application No. 61/537,856, filed Sep. 22, 2011, U.S. Provisional Patent Application No. 61/618,307, filed Mar. 30, 2012, and U.S. Provisional Patent Application No. 61/636,411, filed Apr. 20, 2012, and is a continuation-in-part of International Application No. PCT/US12/28522, filed Mar. 9, 2012, which claims the benefit of U.S. Provisional Patent Application No. 61/451,903, filed Mar. 11, 2011, U.S. Provisional Patent Application No. 61/537,856, filed Sep. 22, 2011, U.S. Provisional Patent Application No. 61/538,558, filed Sep. 23, 2011, and U.S. Provisional Patent Application No. 61/550,516, filed Oct. 24, 2011, the contents of each of which are incorporated herein by reference in their entireties.

TECHNICAL FIELD

The present disclosure is generally directed to systems and methods for washing biological cells. More particularly, the present disclosure is directed to the sterile sequential processing of biological fluid and washing of biological cells using one or a series of disposable fluid circuits and a reusable processing apparatus in a closed system or environment. The present disclosure is also directed to systems and method for washing biological cells with on-line dilution of the cell feed to prevent inadvertent target cell loss.

BACKGROUND

The processing of biological fluid such as blood or blood components typically involves using a reusable processing apparatus ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

The disposable fluid circuits typically include plastic containers and tubes that are pre-connected, pre-assembled, and pre-sterilized, such as by radiation or steam sterilization. In some processing systems and methods, containers including liquids such as anticoagulant, saline, wash solution, storage media, or treating agents may likewise be pre-attached to the disposable fluid circuit, thereby creating a "closed" system. A "closed" system is one where the interior of the system, i.e., internal flow paths, separation chambers, etc., are not exposed or "opened" to the outside environment.

However, for a variety of reasons (e.g., sterilization incompatibility, timing of the different phases of the processing methods, sequence of processing and/or treating steps), not all such liquids may be pre-attached to the disposable fluid circuit. In certain, more complex biological fluid processing systems and methods, treating agents or other fluids necessary in the treatment of a given biological fluid or biological cell product may require separate attachment to the disposable fluid circuit at the time of use. In addition, in such more complex biological fluid processing systems and methods, two or more fluid circuits may be used in sequence to carry out the processing and/or treatment, and products collected using one circuit may need to be connected to a second circuit while maintaining sterility of the overall process.

Thus, it would be desirable to provide a series of fluid circuits that allow for the sequential, sterile (i.e., in a "closed" or functionally closed system) processing of a biological fluid and/or desired biological cell population or product. More particularly, it would be desirable to provide a series of disposable fluid circuits which are compatible with one another and allow for sterile connection of selected containers from one circuit to another circuit, as well as to certain auxiliary container processing sets. It would be desirable to provide for a series of fluid circuits that are compatible with and adapted for sequential use with a single reusable apparatus. The reusable apparatus may be pre-programmed to allow for the automated processing of biological fluid and/or biological cell product with each of the circuits of the series of disposable fluid circuits, as well as with any auxiliary container sets.

Where the biological cells are separated using a separation membrane, such as, but not limited to, a spinning membrane, the systems utilizing such membranes may on occasion be subject to increases in pressure. Certain increases in pressure may be caused by the build-up of cellular material at the membrane surface, leading to a reduced yield of the target cells. Thus, it would be desirable to provide a system that prevents inadvertent target cell loss.

SUMMARY

In one aspect, the present disclosure is directed to the system for the treatment of biological fluid. The system includes a reusable cell processing apparatus including a separator element for receiving a separation device and for effecting the separation of a biological fluid into two or more components. The reusable cell processing apparatus also includes a programmable microprocessor programmed to process biological fluid through a fluid circuit. The microprocessor programmed to instruct the system to deliver a pre-selected volume of diluent to a source of biological fluid. The system further includes a disposable fluid circuit that includes at least one membrane separation device in fluid communication with a first product container and an access device for sterile connection to a source of biological fluid.

In another aspect, the present disclosure is directed to a method for washing biological cells. The method includes obtaining a separator that includes a relatively rotatable cylindrical housing and an internal member wherein the cylindrical housing has an interior surface and the internal member has an exterior surface. The surfaces define a gap there between wherein at least one of the surfaces includes a porous membrane. The method further includes drawing biological cells from a container in flow communication with the separator and diluting the biological cells to a selected volume. Furthermore, the method includes introducing diluted cells into the gap of the separator, rotating at least one or both of the housing and the internal member and separating the cells from the liquid medium to concentrate the cells. The method further includes removing at least some of the concentrated cells from the separator through a first outlet removing some of the separated liquid medium from the separated through a second outlet. The method further includes monitoring the pressure and optionally adjusting the dilution of the cells based on pressure monitoring.

BRIEF DESCRIPTION OF THE FIGURES

FIG. 6 is a perspective view of a separation/washing device using a spinning membrane;

FIG. 7(a) is a perspective view, partially broken away, of the separation/washing of FIG. 6;

FIG. 7(b) is a cross-sectional view of the separation device of FIG. 7(a);

FIG. 8 is a schematic view of an auxiliary container set for use in combination with one or more of the disposable fluid circuits of FIGS. 1-4;

FIG. 9 is a schematic view of a further auxiliary container set for use with one or more of the disposable fluid circuits of FIGS. 1-4;

FIGS. 11(A)-(C) show the steps of providing a treating agent and carrier solution to a disposable fluid circuit in a sterile manner;

DETAILED DESCRIPTION

Figure 1:
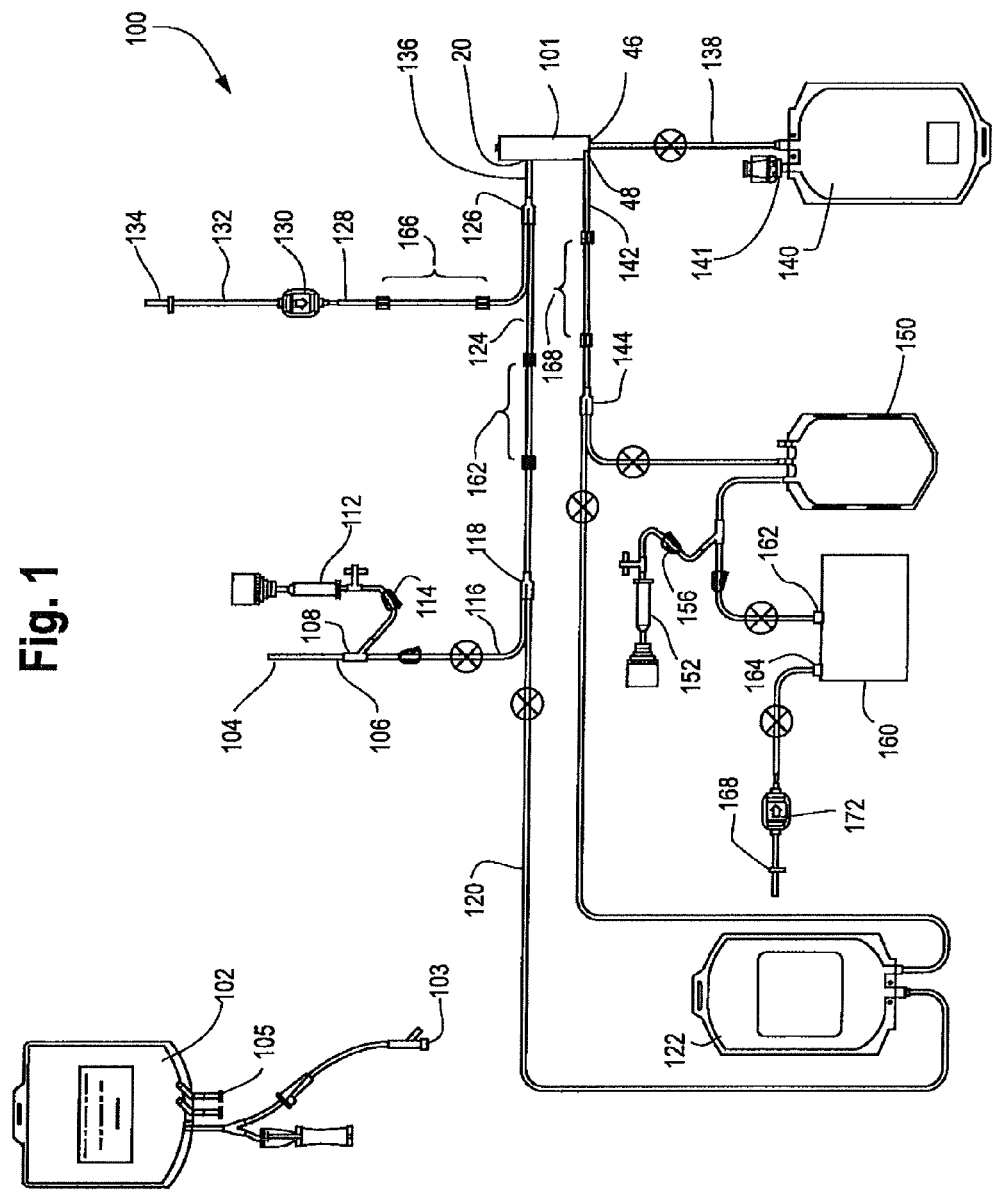
FIG. 1 is a schematic view of one embodiment of a disposable fluid circuit useful in the systems and methods described herein.

Systems and methods for the automated sequential sterile processing of biological fluid are disclosed herein. The systems disclosed typically include a reusable separation apparatus and one or more disposable processing circuits adapted for association with the reusable apparatus. The reusable separation apparatus may be any apparatus that can provide for the automated processing of biological fluid. By "automated," it is meant that the apparatus can be pre-programmed to carry out the processing steps of a biological fluid processing method without substantial operator involvement. Of course, even in the automated system of the present disclosure, it will be understood that some operator involvement will be required, including the loading of the disposable fluid circuits and entering processing parameters. Additional manual steps may be required as well. However, the reusable apparatus can be programmed to process biological fluid through each of the disposable circuits described below without substantial operator intervention.

The reusable processing apparatus is typically capable of effecting the separation of a biological fluid that includes biological cells into two or more components or fractions. Thus, the reusable apparatus may generate conditions which allow for the separation of a biological fluid into selected components or fractions. In accordance with the present disclosure, one preferred means for separating biological fluid into its constituent components or fractions is an apparatus that uses a spinning porous membrane to separate one component from other components. An example of such apparatus is the Autopheresis C® sold by Fenwal, Inc. of Lake Zurich, Ill. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which is also incorporated herein in its entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each are incorporated herein by reference. The references identified above describe a membrane covered spinner having an interior collection system disposed within a stationary shell. While a detailed discussion of the separation device is beyond the scope of this application, the spinning membrane separation device is shown in FIGS. 6, 7(a)-7(b) and is discussed below. In another embodiment, the reusable apparatus may generate a centrifugual field to effect separation.

Turning now to FIGS. 1-4, the systems described herein preferably include two or more disposable fluid circuits for use in the processing of biological fluid. While the circuits described herein may be used as stand alone circuits, more preferably, at least two or more disposable fluid circuits are used in combination and in series for the separation, washing, volume reduction and/or other processing of a biological fluid. As will be apparent from the description and figures below, the circuits used herein share many common elements and as such, where appropriate, identical reference numbers are generally used throughout to refer to identical or substantially identical elements of each of the circuits 100, 100', 100", and 100'''. For example, the circuits 100, 100', 100", and 100''' described below may include an integrated separation device, such as, but not limited to, the spinning membrane 101 (e.g., 101', 101", and 101''') described above. Circuits 100, 100', 100", and 100''' may also include waste container 140, product container 150, and in-process container 122. Disposable fluid circuits of the type described below may further include sampling assemblies 112 and 152 for collecting samples of source biological fluid, "final" product, or other intermediate products obtained during the biological fluid processing.

As will be seen in the Figures and described in greater detail below, the disposable fluid processing circuits include tubing that defines flow paths throughout the circuits, as well as access sites for sterile or other connection to containers of processing solutions, such as wash solutions, treating agents, or sources of biological fluid. As shown in FIGS. 1-4, the tubing of circuits 100, 100', 100", 100''' includes spaced tubing segments identified by reference numerals 162, 166, 168 (and counterpart reference numeral 162', 162", etc.). The tubing segments are provided for mating engagement with the peristaltic pumps of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized polyvinyl chloride. Other useful materials include acrylics. In addition, certain polyolefins may also be used.

As will be apparent from the disclosure herein, source containers may be attached in sterile fashion to each of the circuits 100, 100', 100", and 100'''. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 1 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 1, tubing segment 106 extends from docking site 104 and may optionally include a sampling sub-unit at branched-connector 108. One branch of branched-connector 108 may include a flow path 110 leading to sampling assembly 112. Sampling assembly 112 allows for the collection of a sample of the incoming source fluid. Flow to the sampling assembly 112 is typically controlled by clamp 114. The other branch of branched-connector 108 is connected to and in flow communication with tubing 116. Tubing 116 is connected to further downstream branched-connector 118. Branched-connector 118 communicates with tubing 116 and tubing 120, which provides a fluid flow path from "in-process" container 122, described in greater detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 1, a container of wash or other processing/treating solution may be attached (or pre-attached) to set 100. As shown in FIG. 1, tubing 132 (defining a flow path) preferably includes and terminates in an access site such as spike connector 134. Access site 134 is provided to establish flow communication with a container 135 (shown in FIG. 14) of a wash fluid, such as saline or other solution. Tubing 128 may include an in-line sterile barrier filter 130 for filtering any particulate from a fluid before it enters the flow path leading to second branched-connector 126, and ultimately separator 101. In one embodiment, sterile barrier filter may be a 0.2 μm filter. The wash medium or fluid flows from the wash fluid source through tubing segment 132, where it is filtered by the sterile barrier filter 130 described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. No. 5,194,145 and U.S. Pat. No. 5,053,121, which are incorporated by reference, U.S. Provisional Patent Application Ser. No. 61/451,903 and PCT/US2012/028522, also previously incorporated herein by reference.

As shown in FIG. 1 (and described in greater detail in connection with FIGS. 6, 7(a)-7(d), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container includes a further connection port 141 for sampling or withdrawing the waste from within the product container.

Separation device 101 preferably includes a second outlet 48 that is connected to tubing segment 142 for directing the desired biological cell/fluid product to "final" product container. The other end of tubing segment 142 is connected to branched-connector 144, which branches into and defines a flow path to one or more in-process containers 122 and a flow path to a final product container 150. The final product container 150 may also include a sampling assembly 152. Flow control to the sampling assembly 152 is preferably controlled by clamp 156. The flow path through the access port 154 is controlled by clamp 158.

As further shown in FIG. 1, depending on the processing method and the biological fluid or biological cells being processed, fluid circuit 100 may optionally include an additional chamber for the processing and/or further separation of the biological fluid or cells. As shown in FIG. 1, fluid circuit 100 includes an additional chamber 160 for processing the contents in "final" product container 150. Chamber 160 may be a centrifugal bowl or channel integrally connected to circuit 100. Alternatively, chamber 160 may use a different separation principle (i.e., other than centrifugation) to effect the desired processing of the biological fluid or cells introduced therein. Chamber 160 may include one or more ports 162 and 164 for establishing fluid communication with product container 150 or other container(s) used in the method of processing. For example, port 164 is connected to tubing segment 166 which defines a flow path terminating in access site 168. Access site 168 may be a conventional spike or similar access device adapted for accessing a port of a fluid container including a treating or processing agent. Where access site 168 is a conventional spike, the flow path defined by tubing segment 166 may further include a sterilizing filter 172. Alternatively, access site 168 may be adapted for sterile connection in the manner previously described.

As noted above, chamber 160 is integral with disposable fluid circuit 100 and allows for further processing of the fluid/cells collected in product container 150. In one embodiment, chamber 160 may be a bowl or other container adapted for use with a centrifuge device. An example of such a chamber is provided in U.S. Pat. No. 5,663,051, the contents of which are incorporated herein by reference. Chamber 160 may be disconnected from circuit 100, placed inside a centrifuge device, and subjected to a centrifugal field where the biological fluid/cells may be separated into desired components or fractions.

Figure 2:
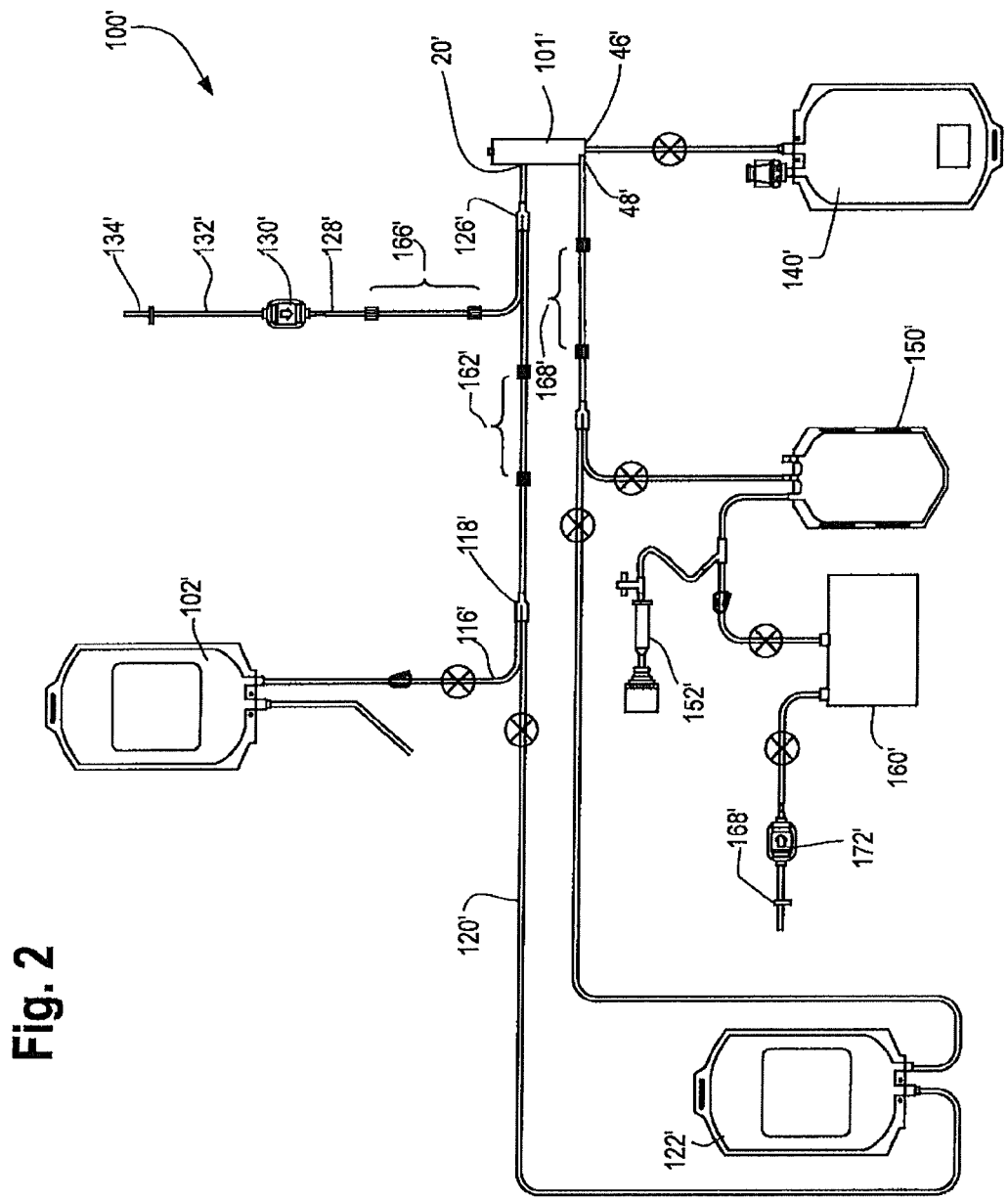
FIG. 2 is a schematic view of another embodiment of a disposable fluid circuit useful in the systems and methods described herein.

Turning now to FIG. 2, disposable fluid circuit 100' includes many of the same elements and is substantially similar to fluid circuit 100 of FIG. 1. Thus, for example, fluid circuit 100' includes a separation device 101', waste container 140', final product container 150', in-process container 152', and an added separation chamber 160', as shown and described above. Disposable fluid circuit 100' also includes a sampling assembly 152' between separation chamber 160' and product container 150'. Tubing and access sites are also provided substantially, as shown, with respect to the disposable fluid circuit 100 of FIG. 1.

Figure 3:
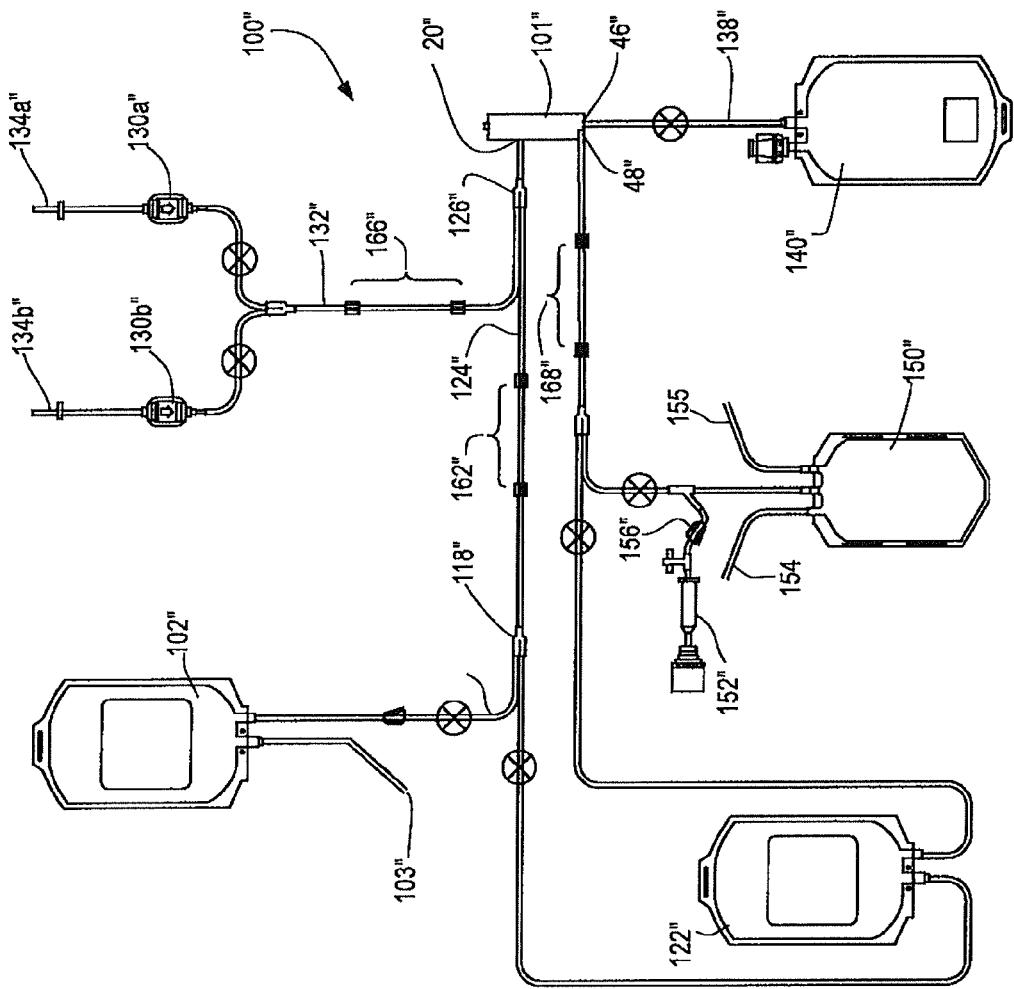
FIG. 3 is a schematic view of yet another embodiment of a disposable fluid circuit useful in the systems and methods described herein.

Turning now to FIG. 3, a further disposable fluid circuit 100" is also shown. Again, as with the disposable fluid circuit of FIG. 2, circuit 100" likewise includes many of the same elements, connections, access sites, sampling assemblies and containers, as previously described with respect to circuits 100 and 100'. As shown in FIG. 3, in one embodiment, fluid circuit 100" is devoid of separation chamber 160 or 160'. Instead, final product container 150" may include a port with a tube extending therefrom terminating in a docking site for attachment to another auxiliary container set or other containers used in the method of processing biological fluid. In addition, fluid circuit 100" may include dual access sites 134a" and 134b". Dual access sites are optional and may be provided for the addition of selected carrier and/or wash solutions in connection with one method of processing. Fluid processing circuit 100" may also include an empty source container 102", which includes a tubing extending from port 103 and terminating in a sterile docking site 103".

Figure 4:
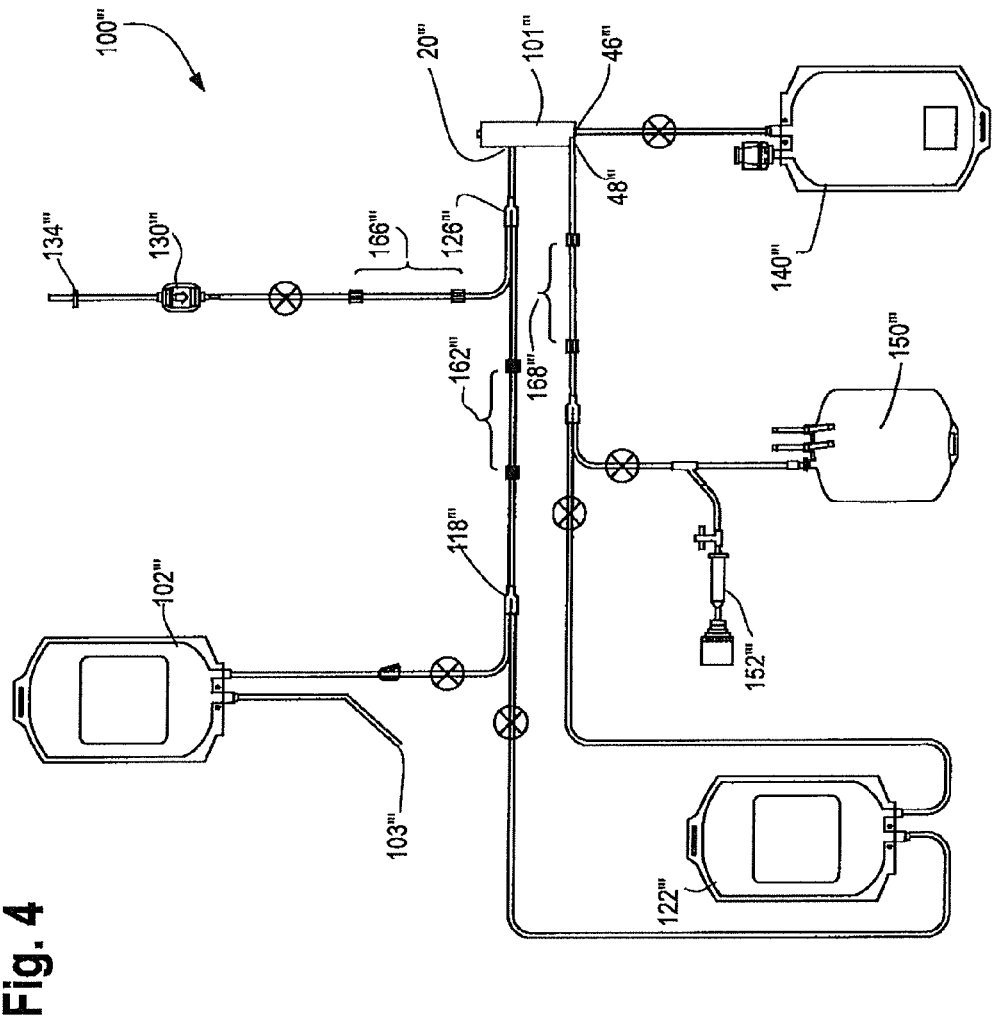
FIG. 4 is a schematic view of still another embodiment of a disposable fluid circuit useful in the systems and methods described herein.

FIG. 4 shows a further disposable fluid circuit 100''', which may also be used in connection with and in conjunction with, or as part of a series of disposable fluid circuits 100, 100' and 100", in accordance with a method for processing biological fluid and/or biological cells. Fluid circuit 100''' likewise includes many of the same elements as the earlier fluid circuits 100, 100', 100", which will not be repeated here. The purpose and function of the various elements will become apparent in connection with the description of an exemplary method of processing biological fluid and/or biological cells set forth below.

Figure 5:
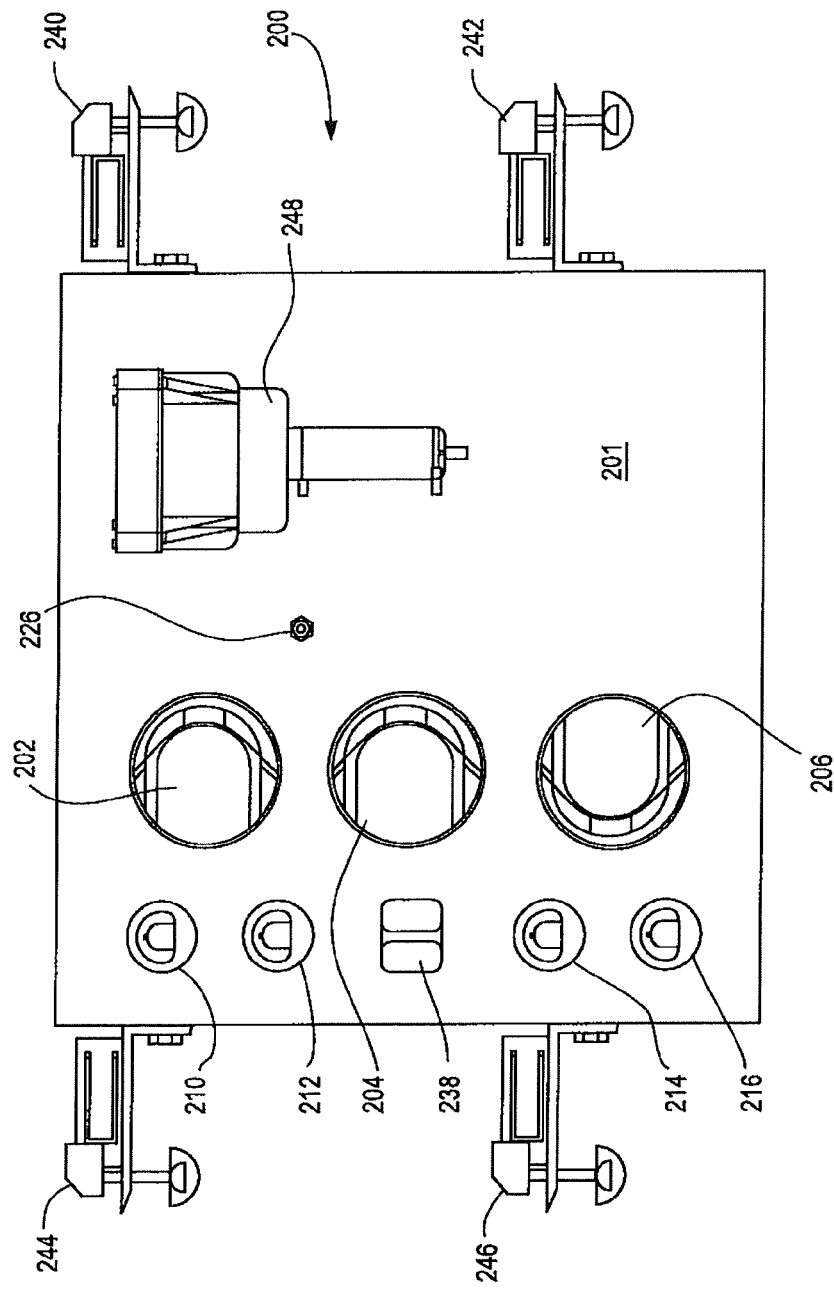
FIG. 5 is an enlarged view of the front panel of the reusable processing apparatus.

FIG. 5 shows the front panel 201 of reusable hardware processing apparatus 200. Apparatus 200 may be of compact size suitable for placement on a table top of a lab bench and adapted for easy transport. Alternatively, apparatus 200 may be supported by a pedestal that can be wheeled to its desired location. In any event, as shown in FIG. 5, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid sets of FIGS. 1-4 at the pump segments identified by reference numerals 162, 166, 168 and advance the cell suspension or other fluid within the disposable set, as will be understood by those of skill in the art. Apparatus 200 also includes clamps 210, 212, 214, and 216. Clamps 210, 212, 214, and 216 are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set "100" at certain points to monitor the pressure during a procedure. Pressure transducer 226 may be integrated into an in-line pressure monitoring site (at, for example, tubing segment 136), to monitor pressure inside separator 101. Air detector 238 sensor may also be associated with the disposable set 100, as necessary. Air detector 238 is optional and may be provided to detect the location of fluid/air interfaces.

Apparatus 200 includes weight scales 240, 242, 244, and 246 from which the final product container, in-process container, source container, and any additional container(s), respectively, may depend and be weighed. The weights of the bags are monitored by weight sensors and recorded during a washing or other procedure. From measurements of the weight sensors, the device determines whether each container is empty, partially full, or full and controls the components of apparatus 200, such as the peristaltic pumps and clamps 210, 212, 214, 216, 218, 220, 222, and 224.

Apparatus 200 includes at least one drive unit or "spinner" 248, which causes the indirect driving of the spinning membrane separator 101 (101', 101" or 101'). Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Turning to FIGS. 6, 7(a) and 7(b), a spinning membrane separation device, generally designated 101, is shown. Such a device 10 forms part of each of the disposable circuits 100, 100', 100" and 100'''.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 6. The boundaries of the blood flow path are generally defined by gap 16 between the interior surface of housing 12 and the exterior surface of rotary spinner 14. The spacing between the housing and the spinner is sometimes referred to as the shear gap. In one non-limiting example, the shear gap may be approximately 0.025-0.050 inches (0.067-0.127 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.025 to about 0.075 inches (0.06-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 34.

Cylindrical housing 12 is completed by an upper end cap 40 having an end boss 42, the walls of which are nonmagnetic, and a bottom end housing 44 terminating in a outlet orifice 46 concentric with the central axis.

With reference to FIGS. 7(a) and 7(b), spinner 14 is rotatably mounted between upper end cap 40 and the bottom end housing 44. Spinner 14 comprises a shaped central mandrel or rotor 50, the outer surface of which is shaped to define a series of spaced-apart circumferential grooves or ribs 52 separated by annular lands 54. The surface channels defined by the circumferential grooves 52 are interconnected by longitudinal grooves 56. At each end of the mandrel 50, these grooves 56 are in communication with a central orifice or manifold 58.

Figure 15:
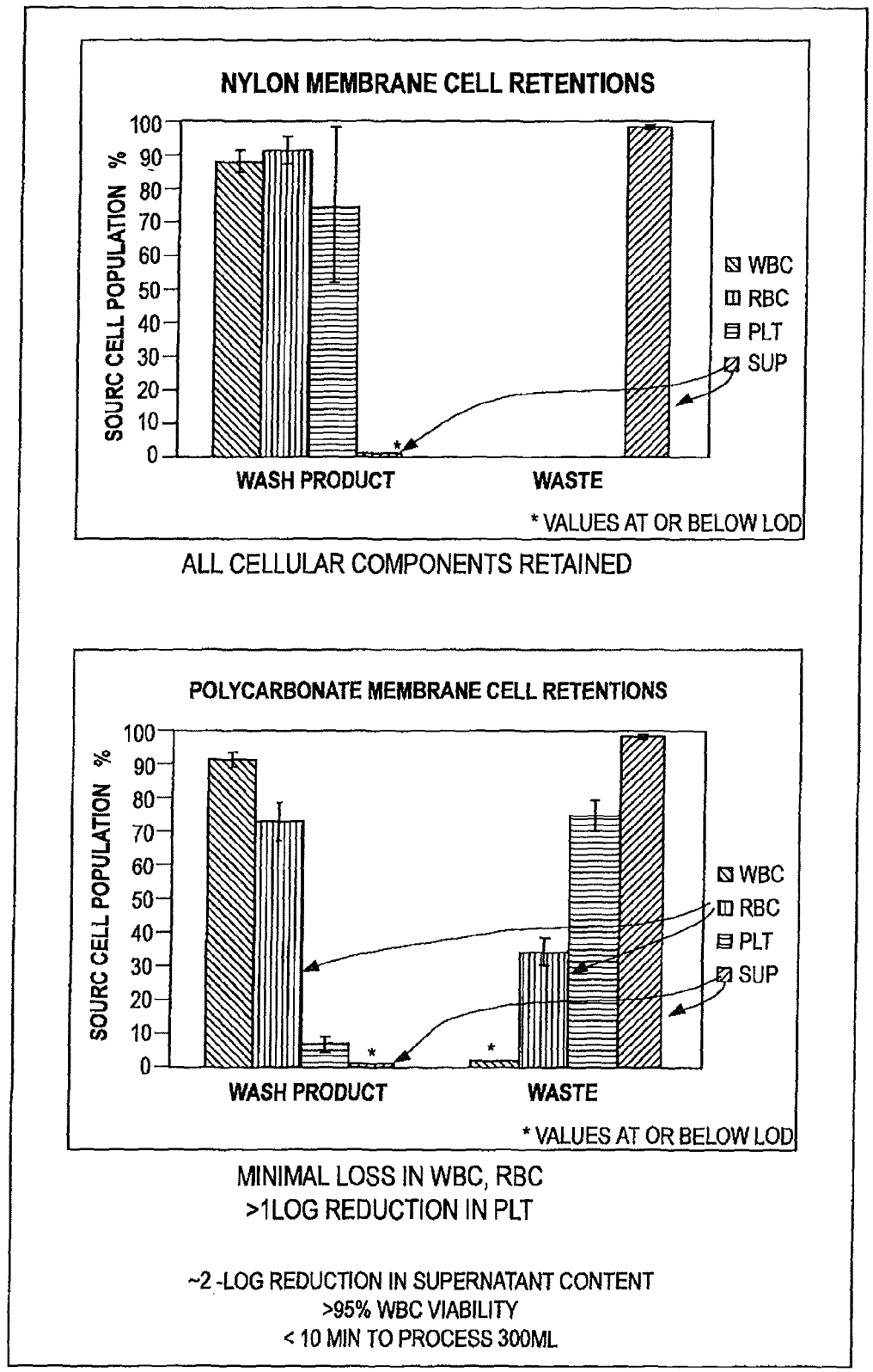
FIG. 15 depicts a pair of graphs showing the cell retention using two different membrane materials for a spinning membrane device.

In the illustrated embodiment, the surface of the rotary spinner 14 is at least partially, and is preferably substantially or entirely, covered by a cylindrical porous membrane 62. The membrane 62 typically has a nominal pore size of 0.6 microns, but other pore sizes may alternatively be used. Membranes useful in the washing methods described herein may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.65 µm and a thickness of approximately 100 µm or greater. Membranes of this type will typically retain all cellular components (e.g., red blood cells, white blood cells) and certain formed blood components, e.g., platelets. In another embodiment, the membrane may be made of a thin (approximately 10-15 micron (µm) thick) sheet of, for example, polycarbonate. In this embodiment, pores (holes) may be cylindrical and larger than those described above. For example, pores may be approximately 3-5 microns (µm), and more preferably about 4 µm. The pores may be sized to allow small formed components (e.g., platelets, microparticles, etc.) to pass, while the desired cells (e.g., white blood cells and larger red blood cells) are collected. FIG. 15 graphically illustrates cell retention with a nylon membrane and a polycarbonate membrane as described above. (The abbreviation "LOD" in FIG. 15 refers to "limits of detection.")

Device 10 is mounted in the upper end cap to rotate about a pin 64, which is press fit into the end cap 40 on one side and seated within a cylindrical bearing surface 65 in an end cylinder 66 forming part of the rotary spinner 14. The internal spinner 14 or outer housing 12 may be rotated by any suitable rotary drive device or system. As illustrated, the end cylinder 66 is partially encompassed by a ring 68 of magnetic material utilized in indirect driving of the spinner 14. A drive motor 70 exterior to the housing 12 is coupled to turn an annular magnetic drive member 72 that includes at least a pair of interior permanent magnets 74. As the annular drive member 72 is rotated, magnetic attraction between the ring 68 interior to the housing 12 and the magnets 74 exterior to the housing locks the spinner 14 to the exterior drive, causing the spinner 14 to rotate.

At the lower end of the rotary spinner 14, the central outlet orifice 58 communicates with a central bore 76 in an end bearing 78 that is concentric with the central axis. An end bearing seat is defined by an internal shoulder 80 that forms a lower edge of a central opening 82. The central opening 82 communicates with the outlet orifice 46. If the inner facing surface of the housing is covered entirely or partially by a membrane, a fluid collection or manifold may be provided beneath the membrane to collect a blood fraction and direct it through a housing outlet (not shown).

U.S. Provisional Patent Application No. 61/537,856, filed on Sep. 22, 2011, the contents of which are incorporated herein by reference, and International Application No. PCT/US2012/028522, filed Mar. 9, 2012, the contents of which are also incorporated herein by reference, disclose methods and systems for washing biological cells using a reusable hardware apparatus and disposable fluid circuit including a spinning membrane separator.

Figure 10A:
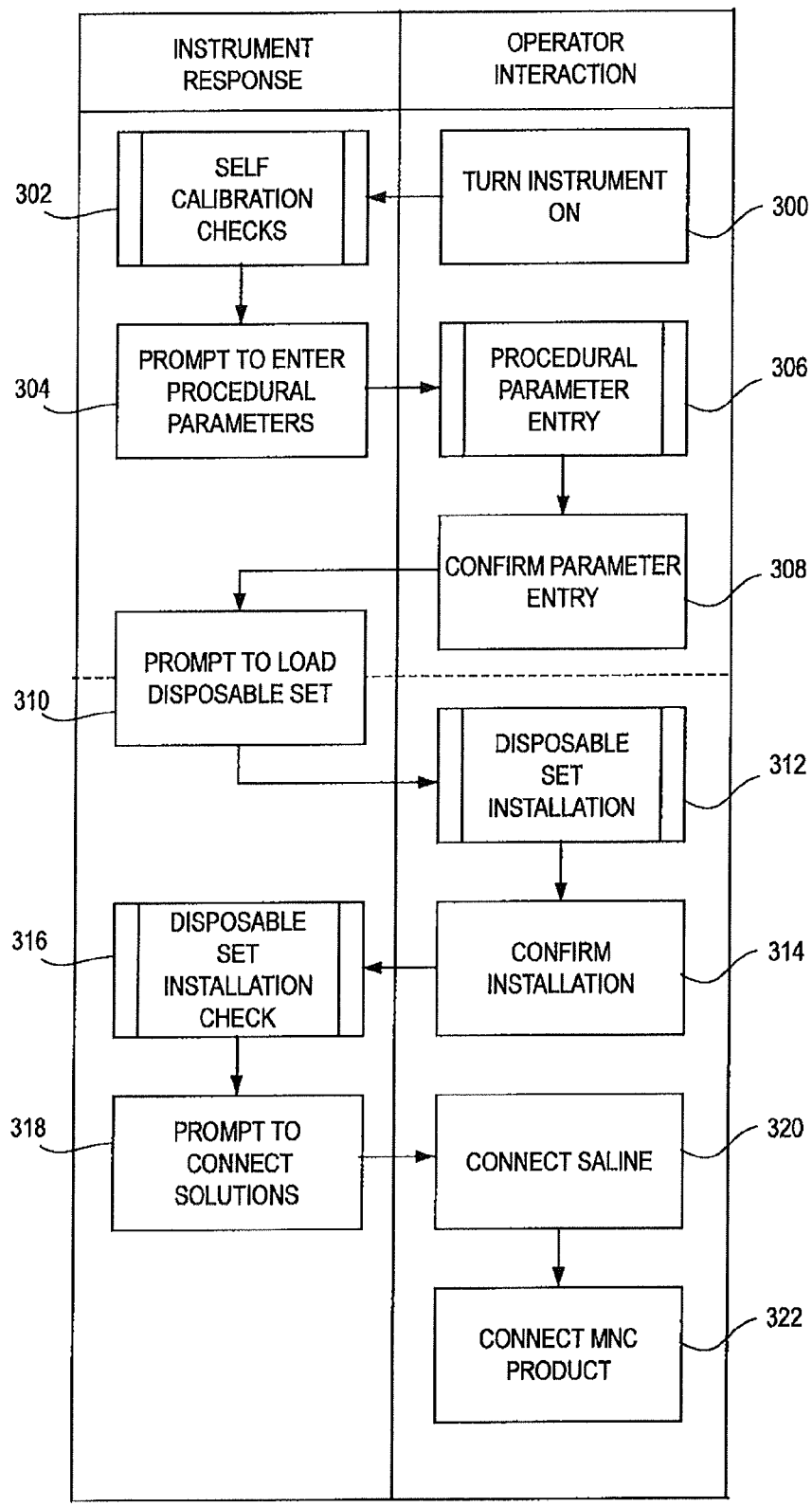
FIGS. 10(a)-10(n) are flow diagrams showing the method steps in one exemplary method of biological cell processing using the reusable processing apparatus and the series of disposable fluid circuits disclosed herein.
Figure 10B:
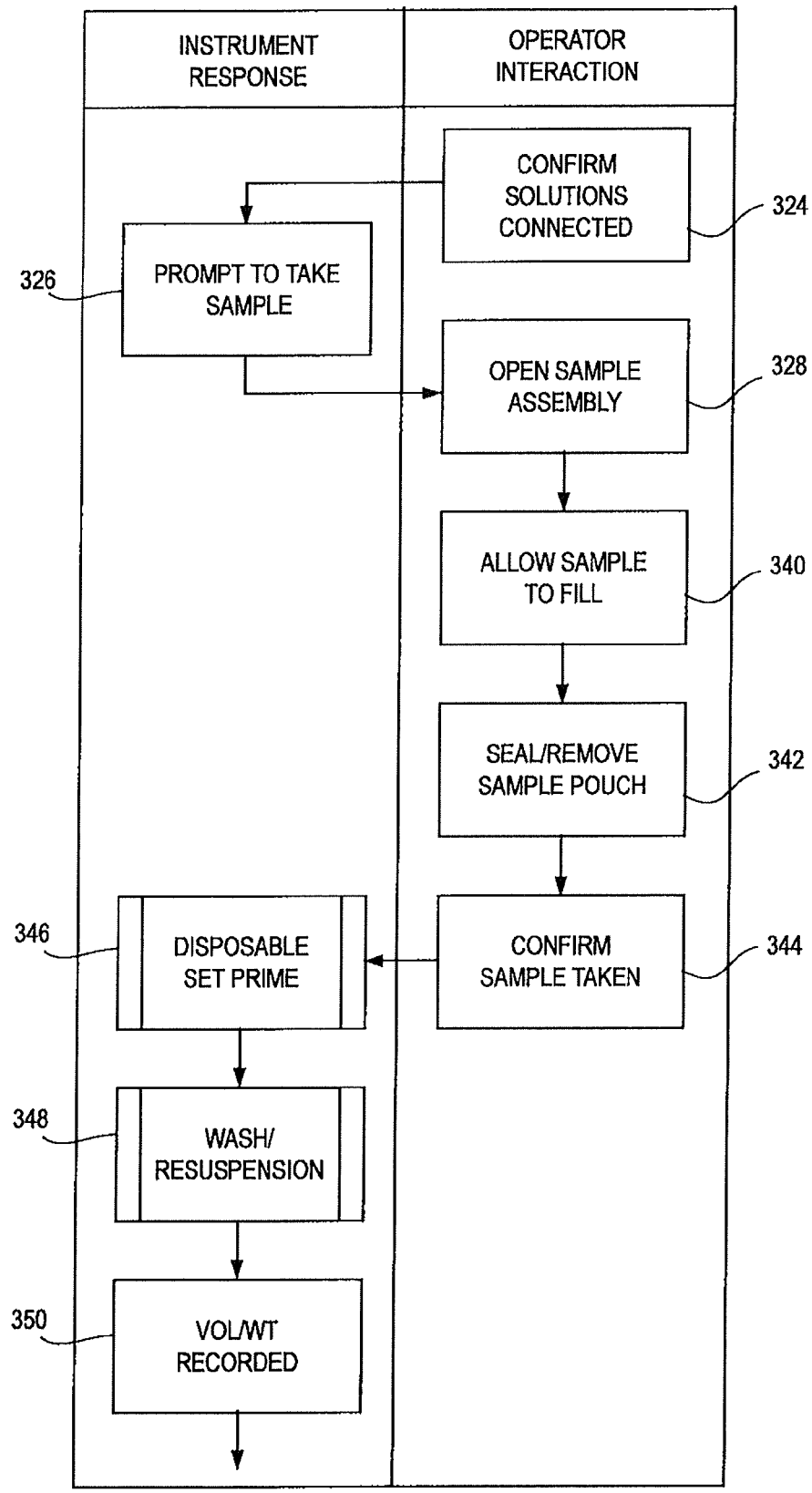
Figure 10C:
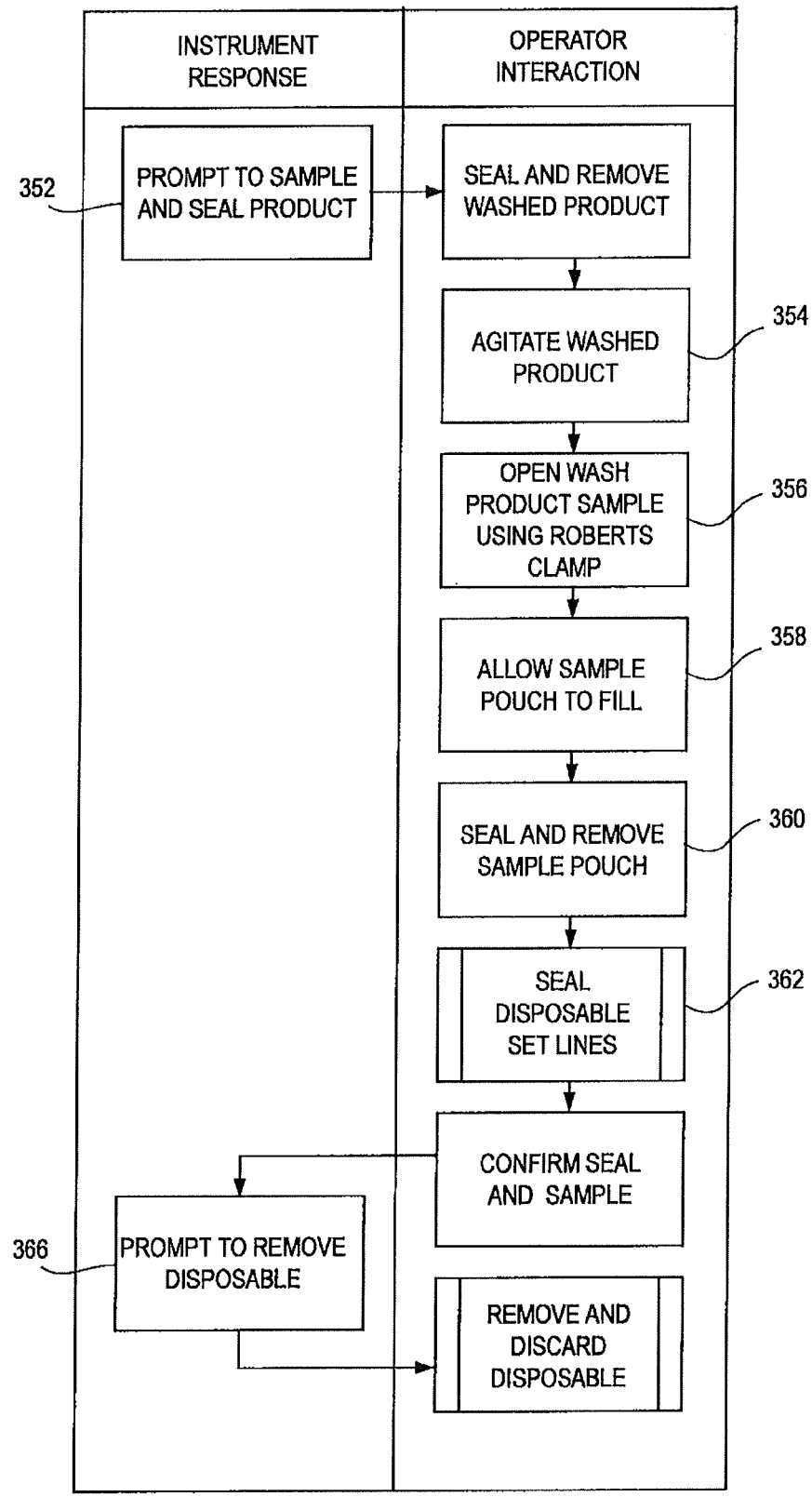
Figure 10D:
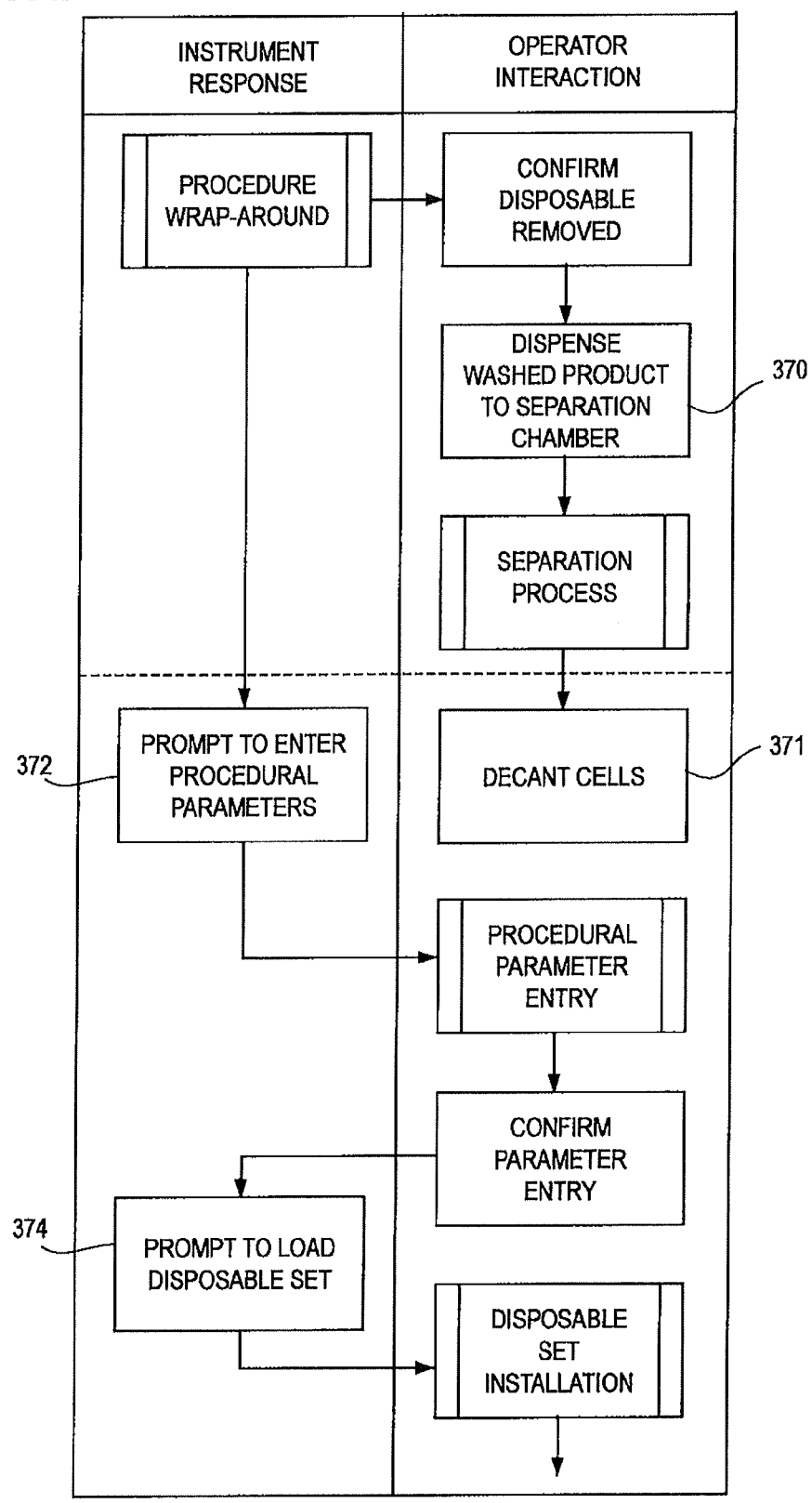
Figure 10E:
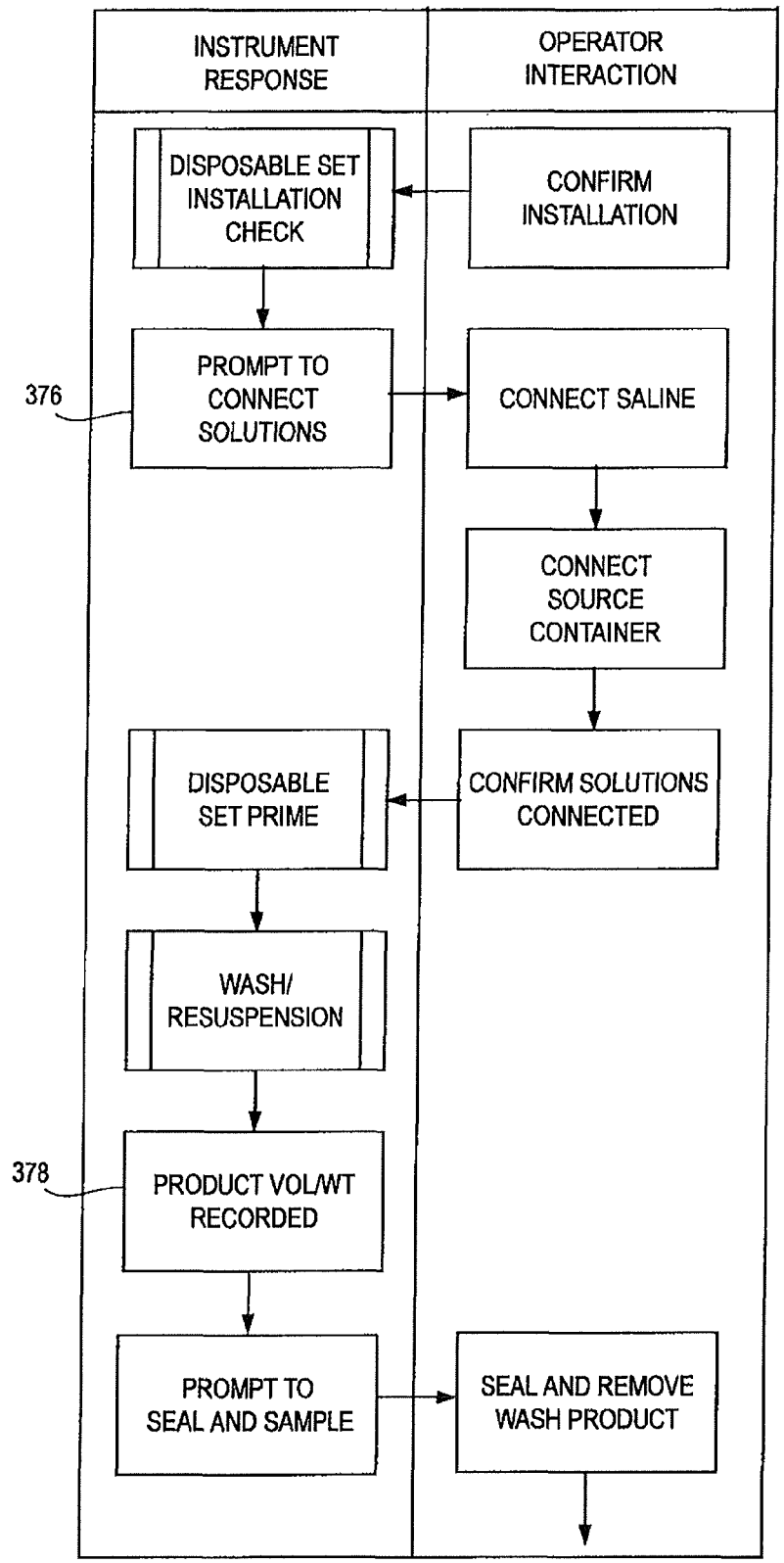
Figure 10F:
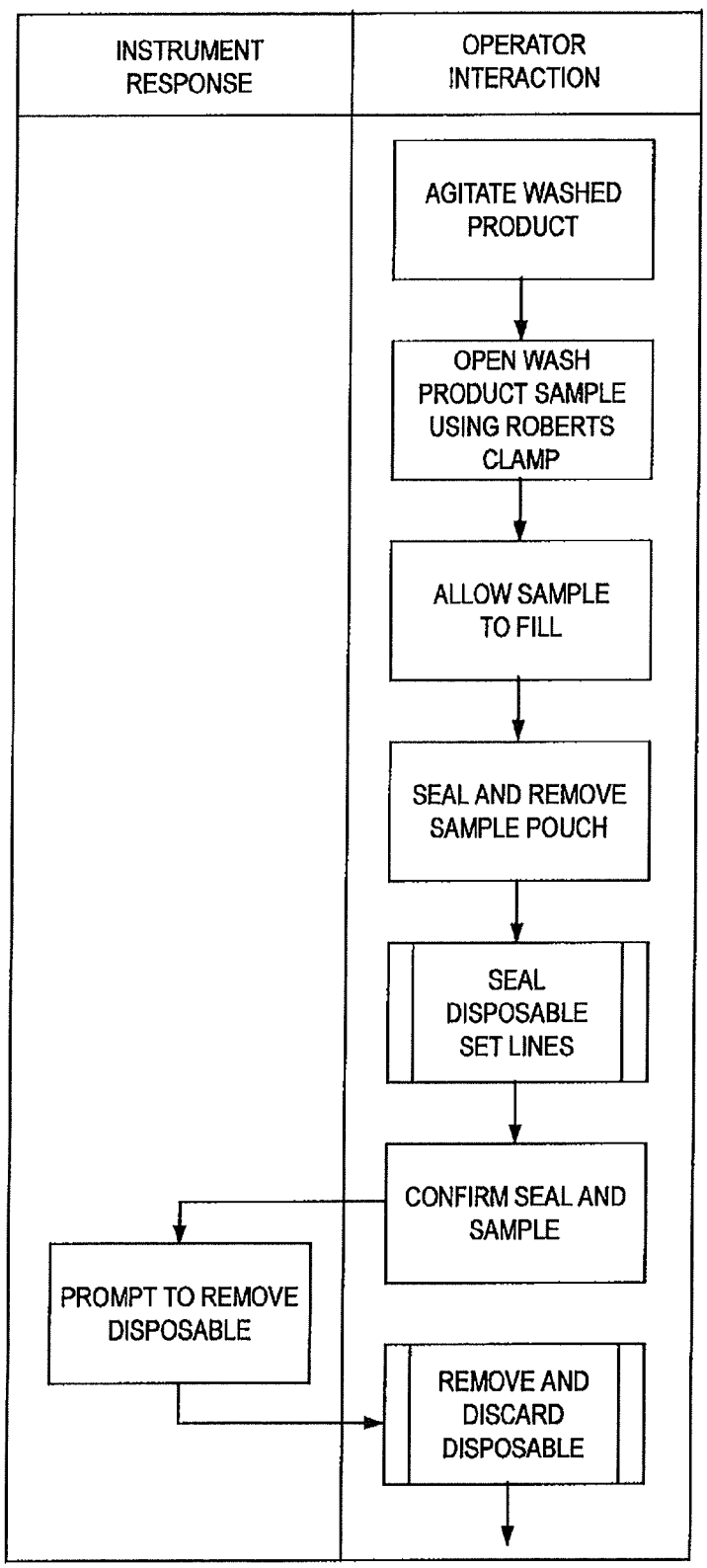
Figure 10G:
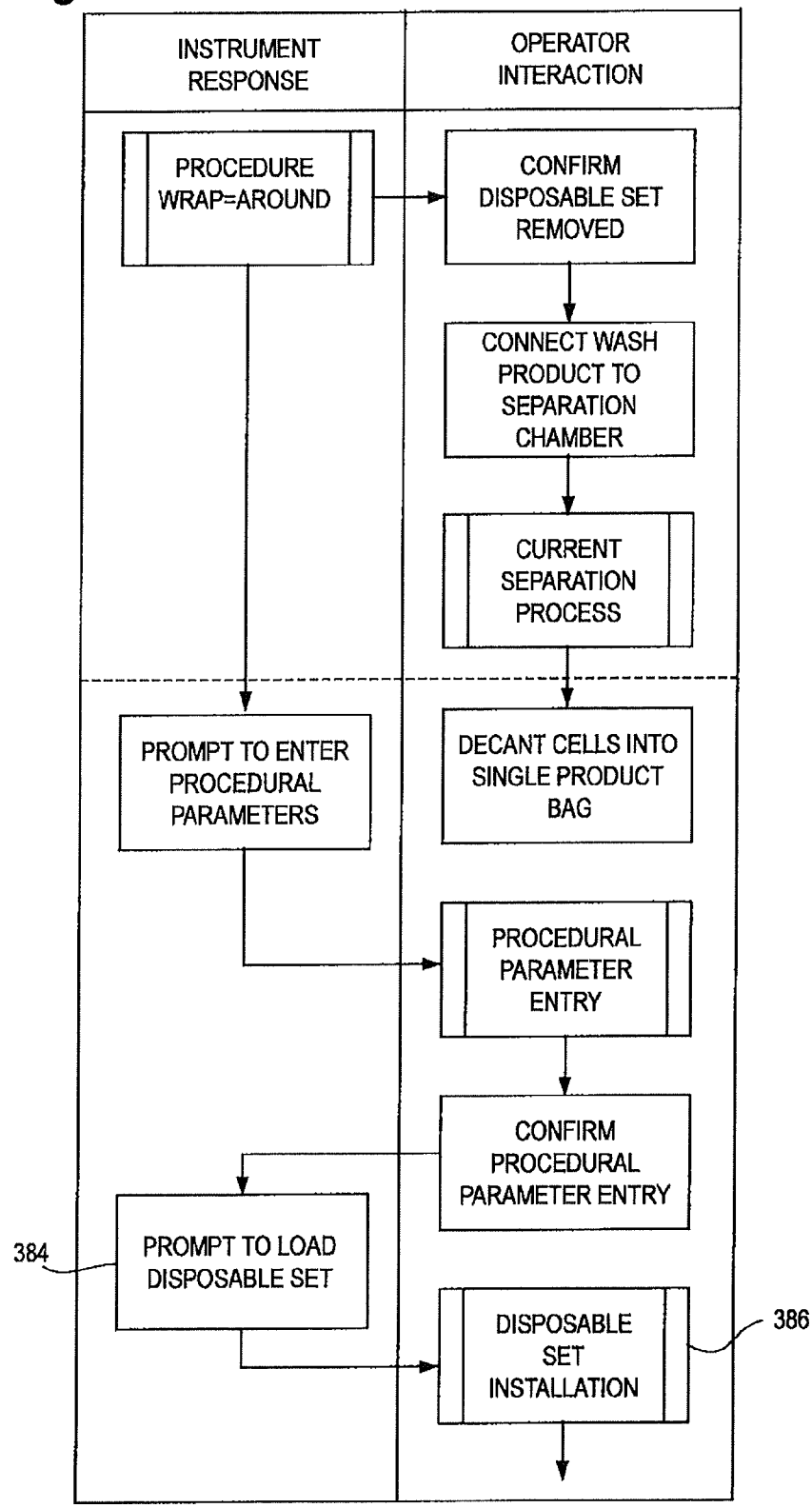
Figure 10H:
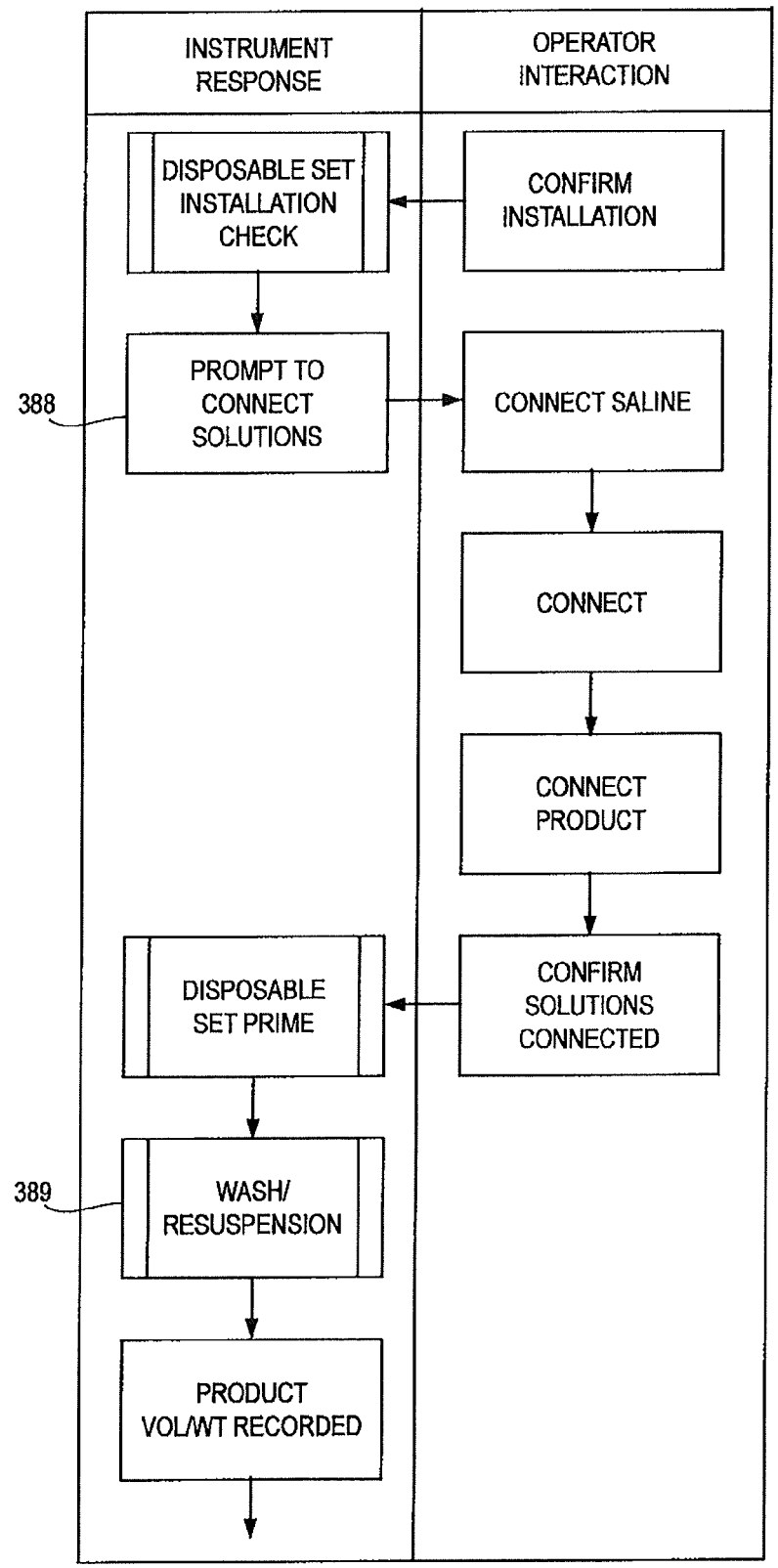
Figure 10I:
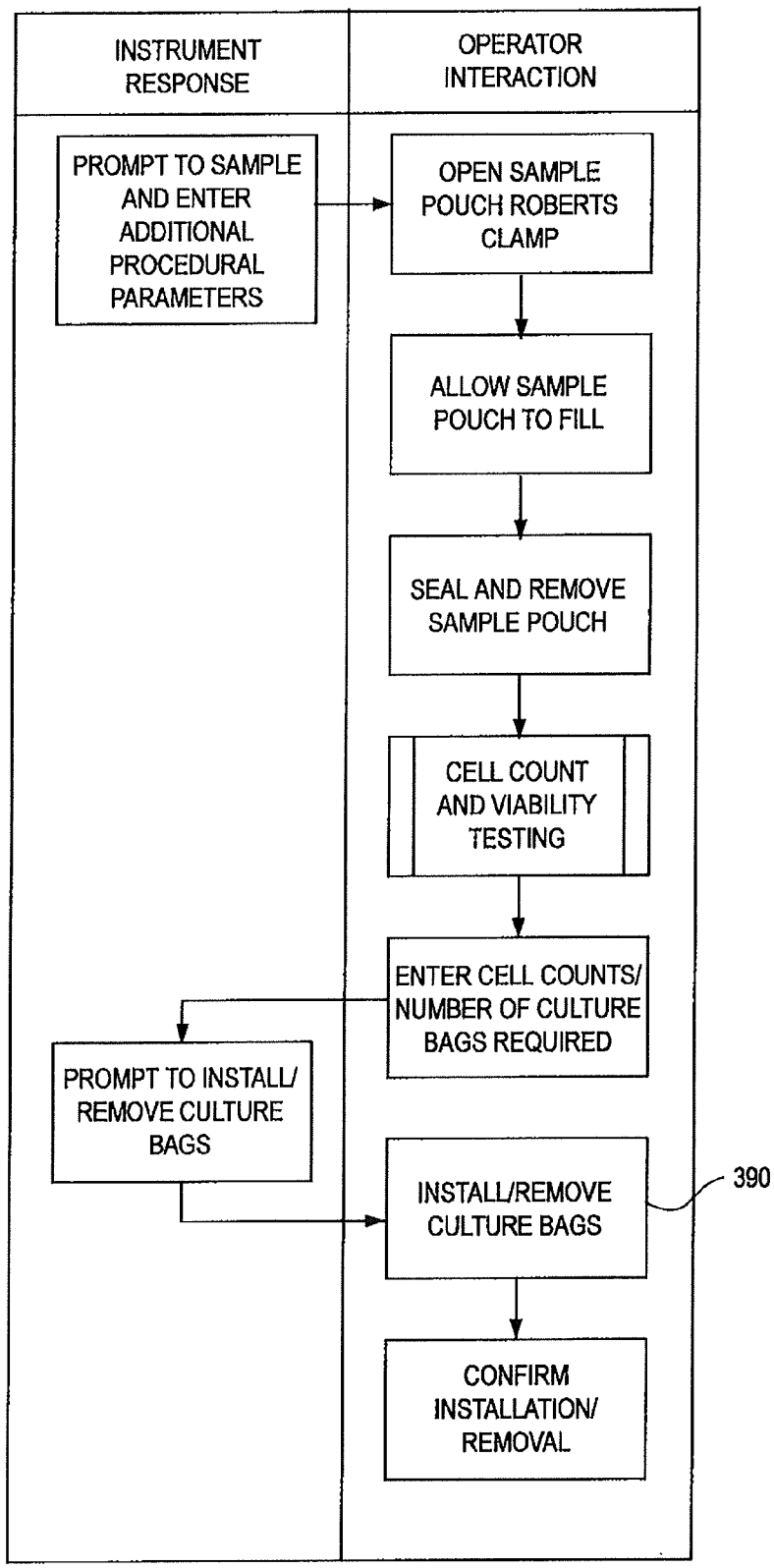
Figure 10J:
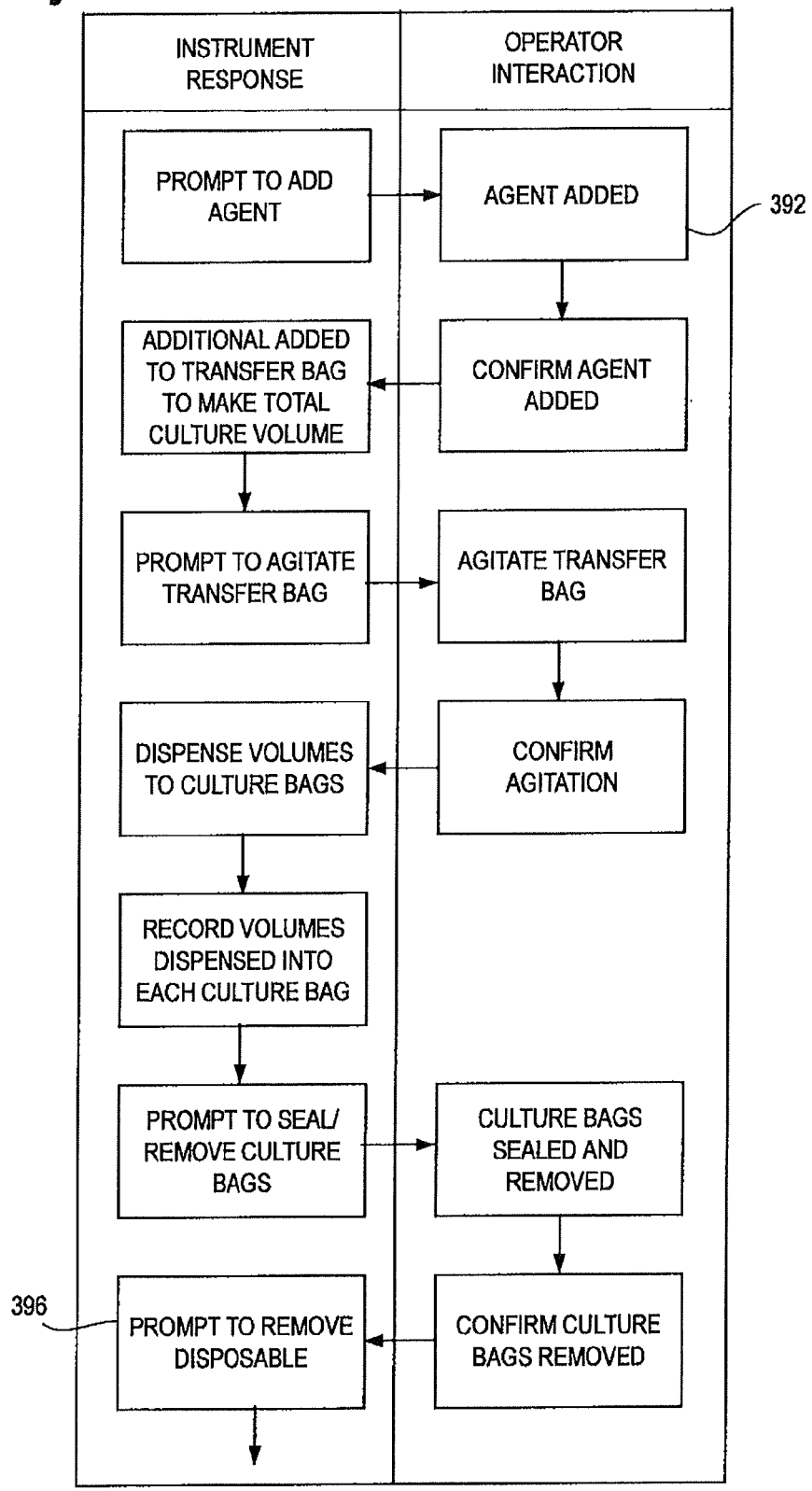
Figure 10K:
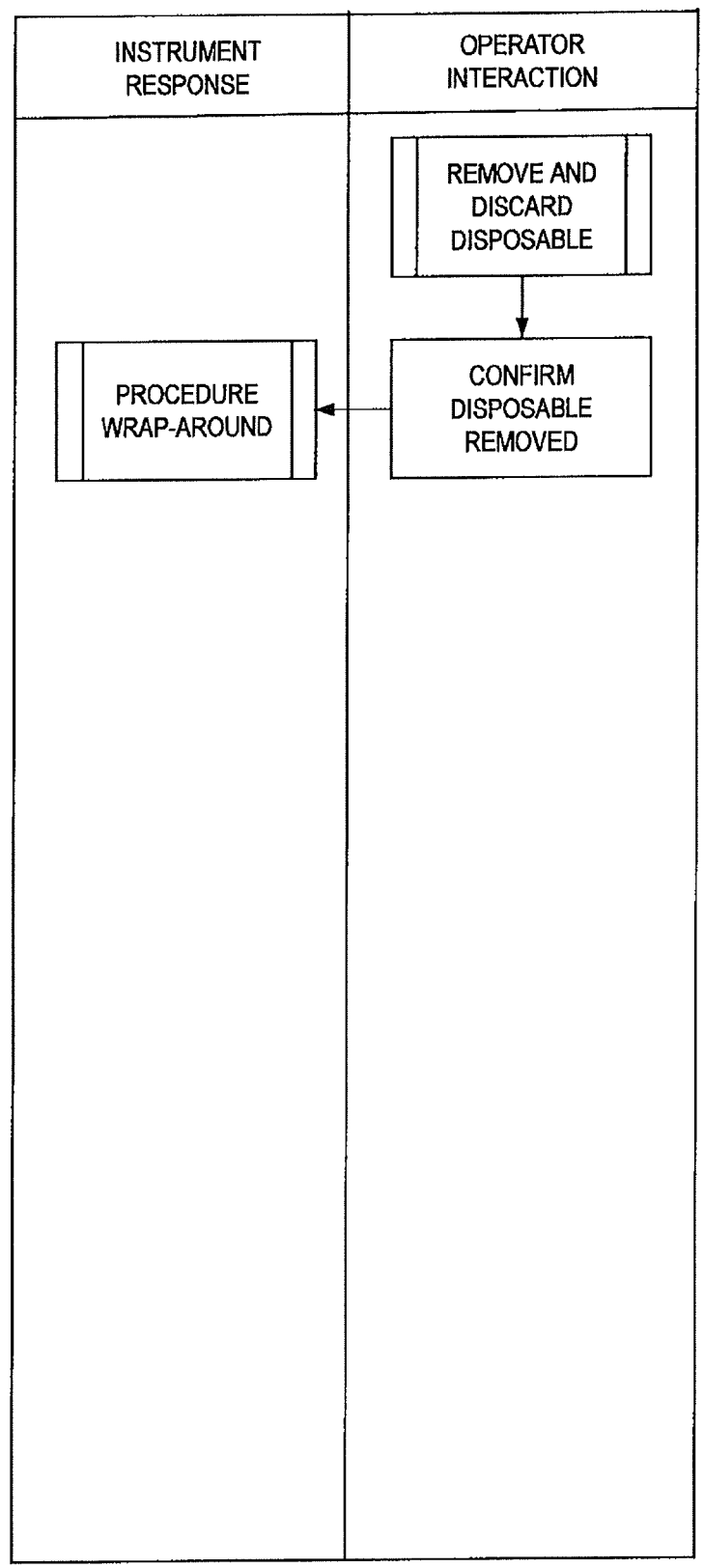
Figure 10I:
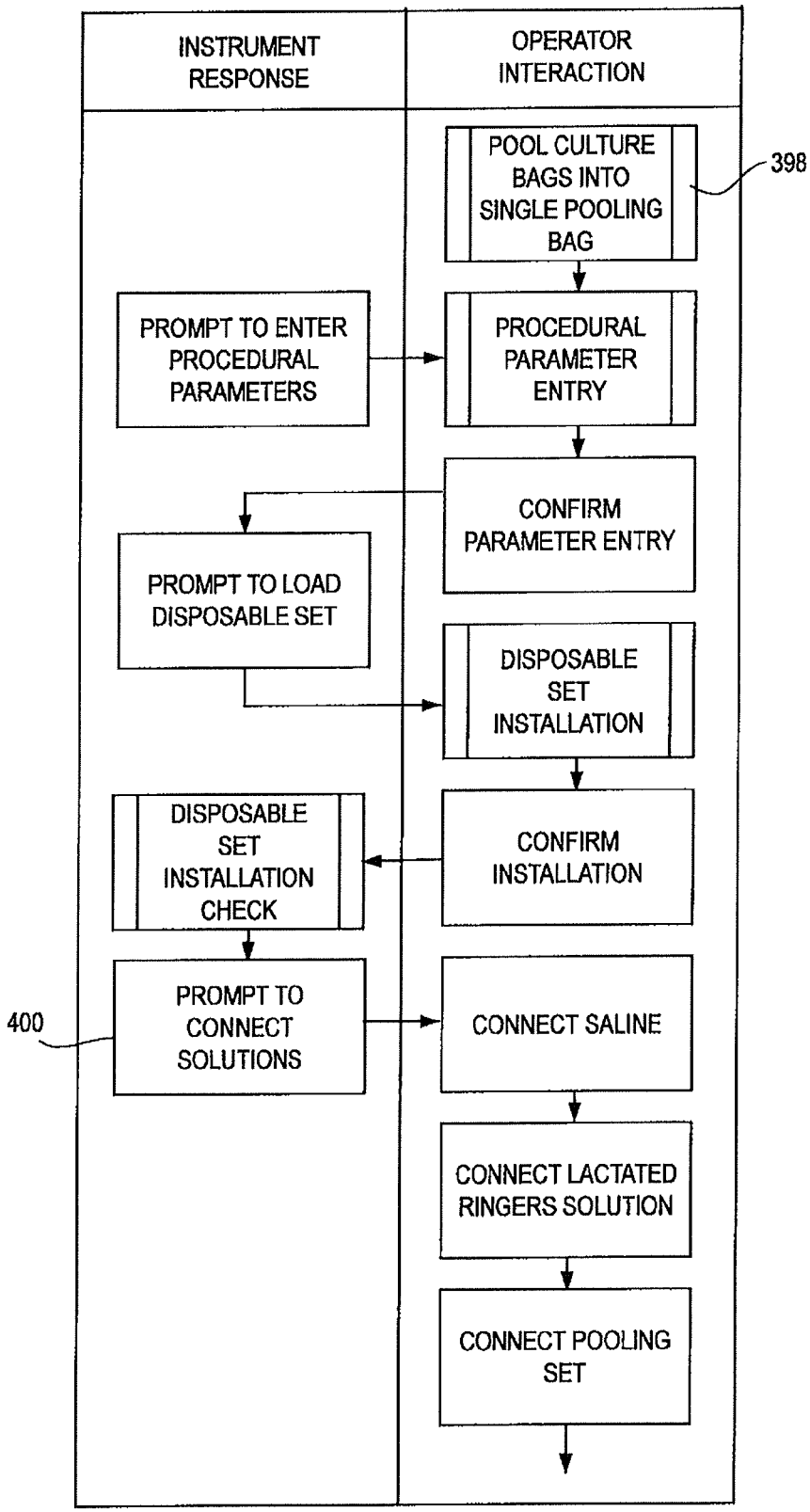
Figure 10M:
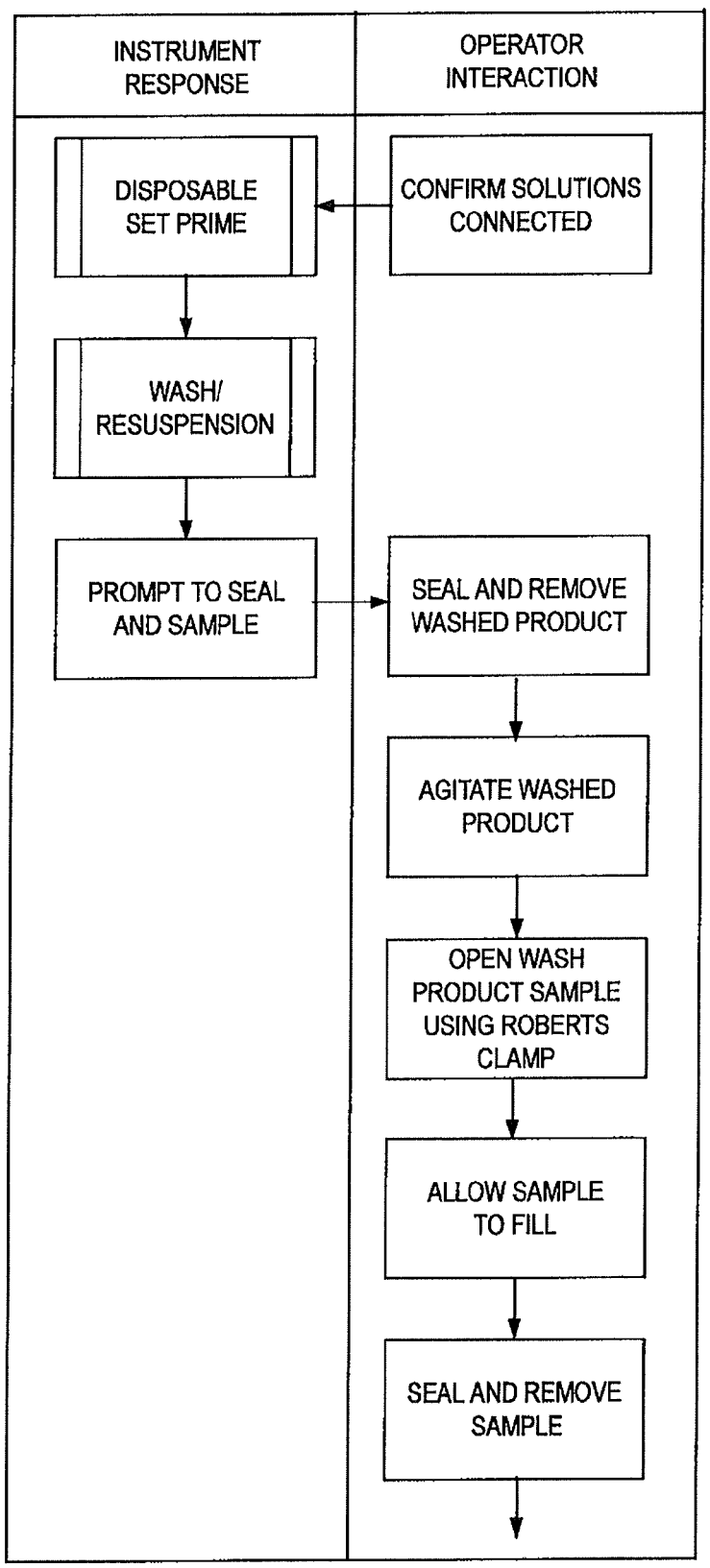
Figure 10N:
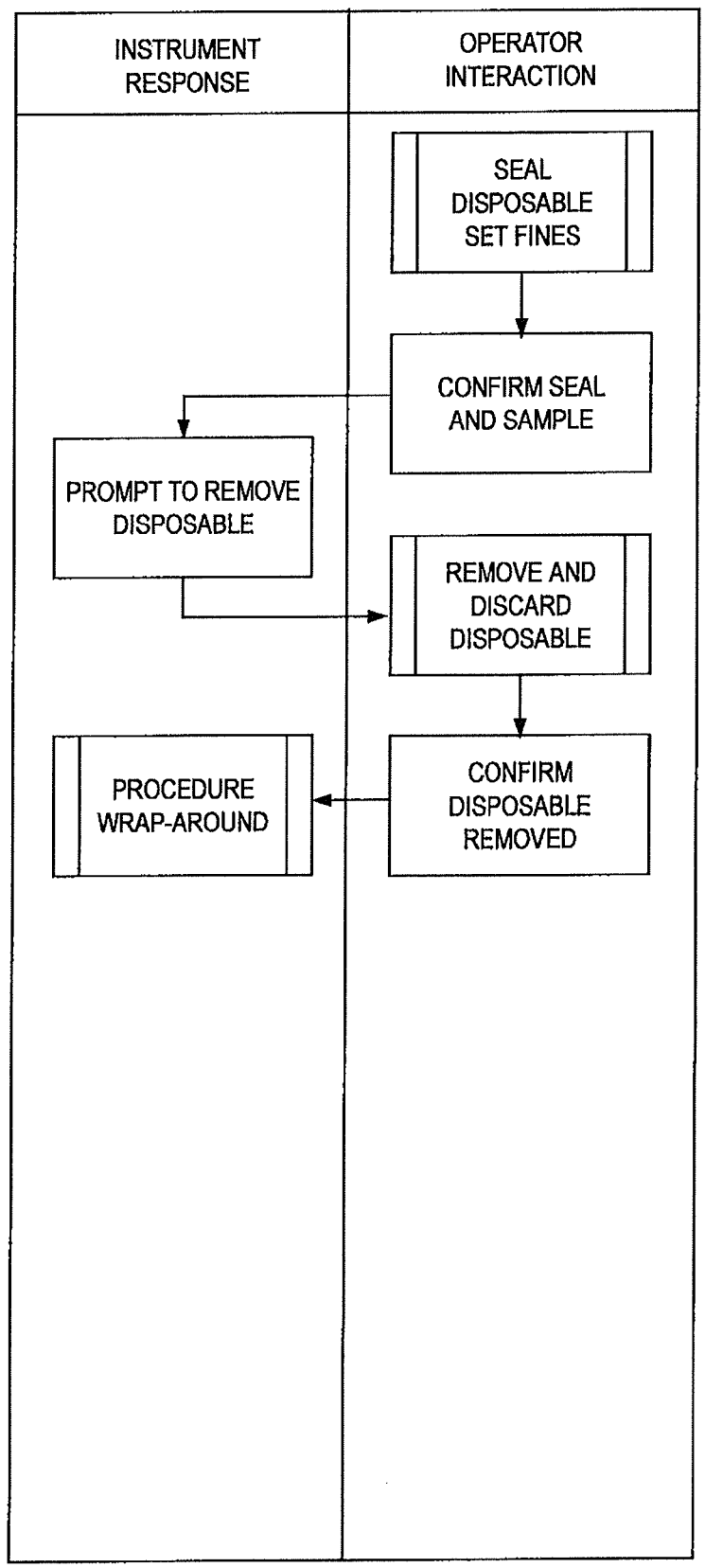

FIGS. 10(a)-10(n) diagrammatically set forth one exemplary and non-limiting method of cell processing (e.g., washing) using a disposable fluid circuit and reusable hardware of the type discussed above. The exemplary method involves the processing, washing, treating and incubating of biological cells, such as mononuclear cells for subsequent therapeutic administration. It will be understood, however, that the method described below is not intended to limit the invention or the use of the system and the fluid circuits described below. Other methods using less than all of the disposable fluid circuits and/or auxiliary container sets, or processing circuits that have been modified, or fewer than all of the enumerated steps may be practiced without departing from the spirit or scope of the present invention.

Many of the steps described below are performed by the software driven microprocessing unit of apparatus 200 with certain steps performed by the operator, as noted. Turning first to FIG. 10(a), the apparatus 200 is switched on at step 300. Apparatus 200 conducts self-calibration checks 302, including the checking of the peristaltic pumps, clamps, and sensors. Apparatus 200 then prompts the user to enter selected procedural parameters (step 304), such as the washing procedure to be performed, the amount of cell suspension to be washed, the number of washings to take place, etc. The operator may then select and enter the procedural parameters for the wash procedure (step 306).

Apparatus 200 (through the controller) confirms the parameter entry 306 and then prompts the operator to load (step 310) the disposable set. The operator then loads the disposable set (step 312) onto the panel of apparatus 200. In one exemplary embodiment, the disposable set may be the fluid circuit of FIG. 1. After installation of the disposable set, apparatus 200 confirms installation as shown in (step 314).

After the disposable set is mounted, apparatus 200 automatically checks to determine whether the disposable set is properly installed (step 316). After apparatus 200 determines that the disposable set is properly installed, the controller prompts the operator to connect the biological fluid and wash medium (step 318). The operator then connects the wash medium (such as, but not limited to saline) (step 320) to the disposable set via a spike connector. The operator then connects source container 102 of the biological fluid or biological cell product (typically derived from an earlier, separate procedure (step 322)) to the disposable set via a spike connector or sterile connection as previously described. In one embodiment, the source of biological fluid/cells may be apheresis-collected mononuclear cells.

As shown in FIG. 10(b), after the source of biological fluid and wash medium are connected to the disposable set, the operator confirms that the solutions are connected (step 324). The device prompts the operator to take a cell suspension sample (step 326). The operator or the device then opens sampling assembly clamp 328 to introduce fluid into the sample chamber of the sampling assembly (step 340). Once the sample chamber is sufficiently filled, it is then sealed and removed (342) from the disposable circuit. The operator confirms (step 344) that a sample has been taken. Following the removal of the sample chamber, the disposable fluid circuit is primed (step 346) for the (initial) wash process. In one embodiment, the circuit may be primed with saline, although other bio-compatible aqueous solutions may also be used.

The controller of separation apparatus then commences the wash process. The biological cells to be washed are transferred from source container (e.g., 102 of FIG. 1) through the disposable set to the spinning membrane separator 101 via the operation of one or more peristaltic pumps 202, 204 and 206. Likewise, the wash medium is delivered from its container, through the disposable circuit to the spinning membrane separator 101. In a preferred embodiment, the original cells of the cell suspension are concentrated and/or collected in either an in-process bag (for further processing) or collected in a final product container 150, while supernatant is separated and removed to waste container 140. In a preferred embodiment, the process provides a final concentrated biological cell product 150 resuspended in approximately 200 ml of the wash (e.g., saline) solution with approximately a 2 log reduction of supernatant contents. If (further) washing or diluting of the cell suspension is necessary, the cell suspension in the in-process bag may be washed (a second time) with the same or different wash medium following the process outlined above. Prior to the conclusion of each wash cycle, the cell suspension volume or weight is measured and recorded (step 350). When the concentration of the cells to wash medium reaches an acceptable level the final product bag is filled.

As shown in FIG. 10(c), once the desired volume of the final product is collected, the control and operation device prompts the operator to sample and seal the final product container (step 352). After sampling, the operator then seals and removes from the disposable circuit the washed cell suspension in the final product container 150. The final product container may then be agitated (step 354). The operator opens the sample chamber by opening the clamp (step 356), and the sample chamber is allowed to fill (step 358). Once the sample chamber is filled, the clamp is closed and the sample assembly is sealed and removed (step 360). The operator then seals the disposable set lines (step 362) and confirms that the product container has been sealed and removed, a sample assembly has been filled and removed, and that the disposable set lines have been sealed 364. The control and operation device then prompts the operator to remove the disposable fluid circuit 100, as shown in step 366. The operator then removes and discards the disposable circuit 100 as shown in step 368. A "procedure wrap around," as referenced in FIG. 10(d) (and elsewhere), refers to when the apparatus has completed one procedure and is ready for a new procedure, restarting at a given state.

As shown in FIG. 1, disposable fluid circuit 100 may include an additional processing/separation chamber 160 integrally connected to the circuit. Chamber 160 may be provided where further processing/separation of the washed product in product container 150 may be required as part of a cell treatment method. Thus, in accordance with one such method, chamber 160 may include an access site for sterile connection to a source of a treating or separation-enhancing agent such as a buoyant density solution (BDS). Such solution may be transferred prior to the sampling step described above. Once the sampling assembly has been removed, washed product from container 150 may be automatically dispensed (step 370) into chamber 160. Once the washed product has been transferred to separation chamber 160, the flow paths between container 150 and chamber 160 may be sealed and chamber 160 may be detached from the remainder of circuit 100. Chamber 160 may then be subjected to a centrifugation step (in a separately provided centrifuge) where the washed biological cell product/BDS suspension is separated into the desired lighter and heavier fractions.

The desired fraction may then be decanted to a separate container (step 371) that will serve as a source container in the further processing of the biological cells. For example, in one exemplary method, the lighter fraction in chamber 160 may be decanted to a source container 102' shown in FIG. 2.

For further processing/washing of the contents of source container 102', the system may again prompt the operator to enter the procedural parameters (step 372), as shown in FIG. 10(d). The system may then prompt the operator to load disposable circuit 100' of FIG. 2 (step 374). Once the operator has installed circuit 100' (and confirmed its installation), the system may prompt the operator to connect the required solutions (step 376). The operator then connects the desired wash solution (e.g., saline) at access site 134' and sterilely connects source container 102' to the terminal end of flow path 106'. As previously discussed, sterile connection may be achieved by employing sterile docking devices, such as the BioWelder, available from Sartorius AG, or the SCD IIB Tubing Welder, available from Terumo Medical Corporation. Other methods of sterilely connecting source container 102' to fluid circuit 100' may be also be used. The system is pre-programmed to prime circuit 100' and then deliver the product from source container 102' and the wash solution to separation device 101'. Waste (supernatant) from the washing step is directed to waste container 140' and the desired cellular product is delivered to product container 150'. The volume/weight of container 150', which is suspended from the system's weight scales (240-248 of FIG. 6) is recorded (step 378) by the system and the operator is then prompted to collect a sample of the washed product.

Sampling may proceed substantially as described in connection with the sampling of washed "final" product in disposable fluid circuit 100. In addition, it will be noted that disposable fluid circuit 100' may also include a pre-connected separation chamber 160'. Chamber 160' may include a flow path extending from an outer port and terminating in an access site for sterile connection to a source of a treating or selected separation-enhancing agent such as a buoyant density solution (BDS). Such solution may be transferred prior to or after (as shown in FIGS. 10(f) and 10(g)) the sampling step described above. Once the sampling assembly has been removed, washed product from container 150' may be automatically dispensed (step 382) into chamber 160'. Once the washed product has been transferred to separation chamber 160', the flow paths between container 150' and chamber 160' may be sealed and chamber 160' may be detached from the remainder of circuit 100'. Chamber 160' may then be subjected to centrifugation or other separation step (in a separately provided centrifuge) where the washed biological cell product/BDS suspension is separated into the desired lighter and heavier fractions.

Following separation of the cell suspension in separation chamber 160', the desired fraction may then be decanted to a separate container that will serve as a source container in the further processing of the biological cells or, more preferably, to an auxiliary container set. An example of an auxiliary container set is shown in FIG. 8. As shown, in FIG. 8, auxiliary container set 500 includes sterile dock access site 502 and at least two containers 504 and 506 in openable flow communication with access site 502 and separated by branch member 508. In accordance with the one embodiment of a method of processing, washing and treating mononuclear cells, auxiliary container set 500 is sterilely joined to chamber 160'. One fraction (e.g., the lighter fraction) may be decanted as waste into one of the containers (e.g., 504), while a resuspending medium (e.g., saline) may be introduced into chamber 160' to resuspend the remaining and desired biological cell product. The auxiliary container set can be disconnected from chamber 160' and the contents of chamber 160' may then be transferred to the next source container 102" shown in FIG. 3.

The system may then prompt the operator to enter the processing parameters (step 384 of FIG. 10(g)) for further processing and to load fluid circuit 100" (of FIG. 3) onto reusable processing apparatus 200 (step 386). Once proper installation of the next in sequence fluid processing circuit has been confirmed, the system will prompt the operator to connect the solutions (step 388), including wash solution (saline) at access site 134a, a carrier solution at access site 134b, and source container 102".

In accordance with one example of a cell processing method (e.g., mononuclear cell processing), the system may be programmed to deliver the contents of source container 102" to separation device 101" with a carrier solution and saline (step 389). Separated biological cells with a carrier solution are collected in product container 150".

As seen in FIG. 3, product container 150" may also preferably include two access sites 154" and 155" for sterile docking. In a specific embodiment of a method for processing cells (such as mononuclear cells), access site 154" may be sterile docked to a further auxiliary set 157, such as the one shown in FIG. 9. Auxiliary container set 157 (FIG. 9) may include one or more culture containers 159a, b, c and d. Access site 155 may be adapted for sterile connection to a container of treating agent 161 (such as an antigen or other agent useful in the culturing and preparation of selected cells) or, more preferably, a container of combined carrier solution and treating agent. In this preferred embodiment, separate addition (and connection) of carrier solution (at access site 134a of circuit 100") and of treating agent can be avoided by providing a container of carrier solution with an appropriate amount of antigen contained therein. This way the combined carrier solution and agent suspension can be sterile docked to access site 155 of product container 150".

The treating agent/carrier solution may be prepared and delivered in the following manner, as depicted in FIG. 11(A)-(C). In one embodiment, a syringe 460 or other delivery device may be used to remove a desired amount of antigen from vial 462 in a controlled environment, such as a Biological Safety Cabinet (BSC) 464 or other similar hood or enclosure. The contents of filled syringe 460 may then be dispensed (still in the BSC or other controlled environment) into container 466 containing the carrier solution. Container 466 may include a port 467 having a pierceable septum which seals after penetration by the needle of syringe 460. Container 466 preferably includes a sealed tubing 469 in openable flow communication with the chamber of container 466. Once the antigen or other agent has been combined with the carrier solution, container 466 may be brought out from the BSC or other controlled environment and joined to fluid circuit 100" and more specifically product container 150" by connecting in sterile fashion (as described above by using a sterile weld device, such as a Terumo SCD IIB welder) tube 469 and access site 155 of product container 150". Once a sterile connection has been made, a flow path between container 466 and container 150" is established. Treating agent (in carrier liquid) may be delivered to the cells in container 150" by gravity flow or by the action of a pump (not shown).

In either embodiment, system may prompt (step 390 in FIG. 10(i)) the operator to sterilely connect auxiliary set 157, as well as prompt the operator to sterilely connect the container (e.g., 466) of treating agent 161 (step 392 in FIG. 10(j)). In a preferred embodiment, based on the composition of the samples collected prior to wash step 389, the system disclosed herein may automatically calculate the amount of product in container 150, the amount of carrier/agent to be added to each of the culture containers, and/or if separately added, the amount of the treating agent (antigen) to be added to the culture containers 159a-d (step 394). After transfer, the operator may further be prompted to seal and remove set 159 and remove circuit 100 (step 396).

In a further processing step, after an appropriate incubation period, the contents of culture containers 159a-d may be pooled in source container 102''' of the disposable fluid circuit 100' of FIG. 4 (step 398, FIG. 10(l)). Specifically, the pooling container set 157 may be sterilely connected to source container 102''' of the disposable fluid circuit 100'''. The operator may be further prompted to connect additional wash solution and ultimate storage solution in step 400. Once the solutions are connected, the system will automatically process/wash the pooled contents of source container 102' in separation device 101''', removing supernatant and collecting the desired biological cells with the storage solution (for example, Ringers lactate) in final container 150'''. The washing process preferably yields a concentrated cell product resuspended in approximately 295 ml of storage solution with approximately a 3.5 log reduction of supernatant. Samples of the contents in final container 150''' may be collected, as previously described and as set forth in FIG. 10(m). The contents of final container 150''' may then be ready for therapeutic administration.

The systems and methods described herein are effective in the washing of cells such as red blood cells and/or white blood cells. In one example of red cell washing, frozen red blood cells may be incubated within a rejuvenating solution such as Rejuvesol. The solution may be sterile docked or otherwise included in the closed system of the disposable processing sets of the type described above. Incubation occurs at approximately 37° C. within the closed system. The treated cells may then be washed with a washing solution such as saline, Adsol or E-Sol (the latter of which are red cell storage solutions) to reconstitute the red blood cells for subsequent storage and transfusion.

Figure 12:
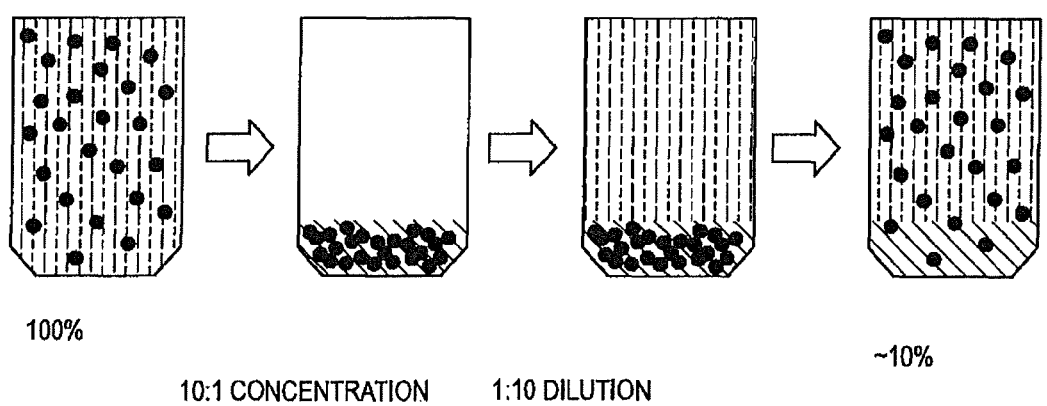
FIG. 12 diagramatically shows the reduction in supernatant content in the biological fluid and cells washed in accordance with the methods and systems disclosed herein.
Figure 13:
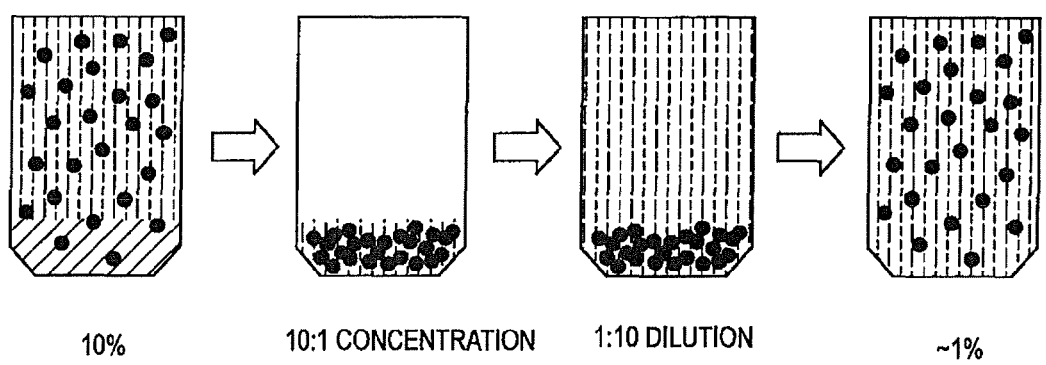
FIG. 13 diagramatically shows the further reduction in supernatant content in the biological fluid and cells washed in accordance with the methods and systems disclosed herein.

The systems and methods described herein are also effective in the reduction of the supernatant volume of the original source of biological fluid. As shown in FIG. 12, supernatant can be reduced to approximately 10% of its original volume (with the optional addition of wash solution). A further reduction the in the supernatant of FIG. 12 can be performed by again concentrating the cells and removing additional supernatant (as shown in FIG. 13) such that the supernatant makes up approximately 1% of the original supernatant volume in the source of biological fluid, or a 2-log reduction in the supernatant. Further reductions are also possible, thus making the system and methods described herein effective in reducing large culture volumes (e.g., 20-40 liters) down to a manageable volume for subsequent administration.

In accordance with another aspect of the present invention, cell washing systems of the type described herein may include a means for preventing inadvertent target cell loss. In one embodiment, preventing target cell loss is achieved by monitoring increases in pressure. Increased pressures may be caused by a cell feed (cell input) having a higher than expected or higher than typical total hematocrit and, more particularly, in the build-up of cellular material on the membrane. Consequently, this may result in a decreased desired cell yield. For example, if the feed concentration is too high such that the retentate concentration exceeds the concentration polarization limit i.e., the limit where boundary formation on the membrane and pressure increases are likely to occur, target cell yield may be reduced.

Figure 14:
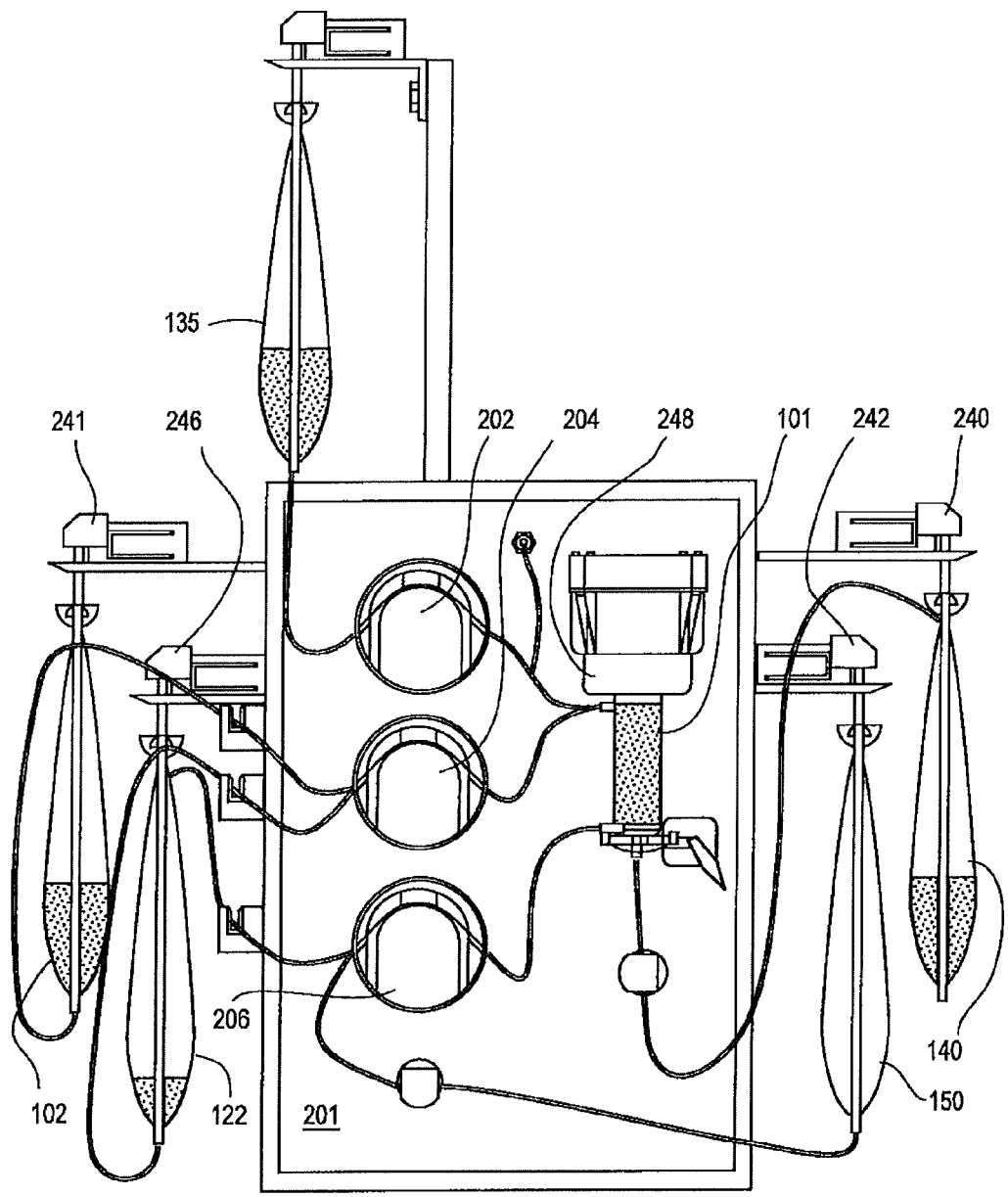
FIG. 14 is another view of the front panel of a reusable processing and/or cell washing apparatus with a disposable fluid circuit loaded thereon.

Accordingly, in an embodiment the system under the direction of the programmable controller may dilute the "feed" entering separator 101 (see FIG. 1) with a selected volume of wash solution 135 (FIG. 14). Dilution of the cell feed from source container 102 reduces the hematocrit of the biological fluid entering separator 101. Inasmuch as the cellular load or total hematocrit of the cell feed may not always be known, in one embodiment, the cell feed is diluted regardless of the cell load. In the event that the cell feed does not have an increased cell load, pressure sensor 226 will record a lower than optimal pressure, allowing the system, under the instruction of the microprocessor, to reduce the volume of diluent to zero. Pressure transducer 226 will continue to monitor the pressure and in response to the pressure reading, cause an increase or decrease of the volume of diluent accordingly. In other words, the volume of diluent may be adjusted accordingly while the system monitors the pressure by pressure sensor or transducer 226 (FIG. 5). In an alternative embodiment, rather than add diluent regardless of the cell load, the system may initially add diluent only in response to a detected increase in pressure.

The initial cell feed may be diluted by combining the feed from container 102 with diluent (wash solution) from container 135 at branched connector 126. In one embodiment, diluent from container 135 may initially be drawn into separator, followed by the cell feed drawn from container 102 and combined with the diluent, as described.

In one example, the pressure will typically not exceed 100 mmHg. The system will initially pre-dilute the cell feed so that the system operates at approximately 100 mmHg. Once this optimal level is reached, the system may slowly decrease the dilution factor used to dilute the feed. In the event that the system registers the pressure that is outside (higher than) the expected system pressure by some selected amount, it can be assumed that the increase pressure was due to the onset of concentration polarization (i.e., formation of the boundary layer). Accordingly, at this point, the system may compensate and adjust the dilution factor so that the feed is below the concentration polarization level. While the system described herein may use a proportional control loop to keep the system pressures below a set pressure point by adjusting the dilution factor, PI, PD or PID controls may also be affected in generating the feedback control loop.

Pressure monitoring may be actuated during the entire procedure using each of the disposable sets described above and shown in FIGS. 1-4. Typically, however, pressure monitoring of the type described above may only be needed during the initial wash using the disposable fluid circuit of FIG. 1. In addition, it will be understood that the pressure monitoring system and on-line dilution described above is not limited to the cell washing system described herein. For example, the pressure monitoring and on-line dilution system may also be used in any cell washing system including a cell washing system of the type described in International application PCT/US12/28522 filed Mar. 9, 2012 and incorporated by reference herein.

In another alternative application of the system and methods described herein, it may be the supernatant that is the desired product. This may be particularly applicable in the field of vaccine production, where it may be desirable to remove the cellular components and retain the supernatant (to produce a vaccine). In this embodiment, what was referenced to as the "waste" container (140, 140', etc.) would, in effect, become a product container.

Thus, an improved system for the sequential washing and processing of biological cells. The description provided above is intended for illustrative purposes only and is not intended to limit the scope of the invention to any specific method, system, or apparatus, or device described herein.

The invention claimed is:

1. A method for washing biological cells comprising:
   obtaining a separator comprising a relatively rotatable cylindrical housing and an internal member, wherein said cylindrical housing has an interior surface and said internal member has an exterior surface, said surfaces defining a gap therebetween, wherein at least one of said surfaces includes a porous membrane;
   drawing biological cells from a container in flow communication with said separator;
   diluting said biological cells with a diluent;
   introducing said diluted cells and diluent into said gap of said separator;
   rotating at least one or both of said housing and said internal member;
   separating said cells from said liquid medium;
   concentrating said cells;
   removing at least some of said concentrated cells from said separator through a first outlet;
   removing at least some of said separated liquid medium from said separator through a second outlet;
   detecting pressure inside of said separator wherein said pressure is based at least in part on the build-up of cellular material on said membrane; and
   adjusting the dilution of said cells if said detected pressure differs from a selected pressure wherein the selected pressure corresponds to a concentration polarization limit.

2. A method for washing biological cells comprising:
   obtaining a separator comprising a cylindrical housing and an internal member, wherein said cylindrical housing has an interior surface and said internal member has an exterior surface including a porous membrane, said surfaces defining a circumferential gap therebetween and about said internal member;
   drawing biological cells from a container in flow communication with said separator;
   diluting said biological cells with a diluent;
   introducing said diluted cells and diluent into said gap of said separator;
   rotating said internal member;
   separating said cells from said liquid medium;
   concentrating said cells;
   removing at least some of said concentrated cells from said gap through a first outlet;
   removing at least some of said separated liquid medium from said separator through a second outlet;
   detecting pressure inside of said separator wherein said pressure is based at least in part on the build-up of cellular material on said membrane; and
   adjusting the dilution of said cells if said detected pressure differs from a selected pressure.

3. The method of claim 2 comprising diluting said biological cells by first introducing said diluent into said separator followed by adding said biological cells to said separator.

4. The method of claim 2 comprising diluting said biological cells by combining said biological cells with said diluent and introducing said combination of cells and diluent into said separator.

5. The method of claim 2 comprising diluting said biological cells only in response to an increase in the detected pressure.

6. The method of claim 2 comprising diluting said biological cells prior to an increase in the detected pressure.

7. The method of claim 2 maintaining the pressure during processing below the selected pressure.

8. The method of claim 2 wherein said diluent is a solution selected for washing biological cells.

9. The method of claim 8 wherein said diluent is saline.

10. The method of claim 2 wherein said diluent is a solution for rejuvenating blood cells.

11. The method of claim 2 wherein said diluent is a solution for storing and preserving blood cells.

12. The method of claim 2 wherein said selected pressure is approximately 100 mmHg.

13. The method of claim 12 comprising reducing the volume of diluent to zero when said detected pressure is below said optimal pressure.

14. The method of claim 2 comprising diluting said biological cells by a dilution factor until a selected pressure is detected.

15. The method of claim 14 further comprising slowly decreasing said dilution factor during said introducing.

16. The method of claim 2 wherein a cellular load of said biological cells is not known, said method further comprising diluting said biological cells regardless of said cellular load.

\* \* \* \* \*